(12) United States Patent
Messersmith et al.

(10) Patent No.: US 10,179,114 B2
(45) Date of Patent: *Jan. 15, 2019

(54) PHENOLIC COATINGS AND METHODS OF MAKING AND USING SAME

(71) Applicant: Northwestern University, Evanston, IL (US)

(72) Inventors: Phillip B. Messersmith, Clarendon Hills, IL (US); Tadas S. Sileika, Northbrook, IL (US); Ran Zhang, Evanston, IL (US); Devin G. Barrett, Evanston, IL (US)

(73) Assignee: Northwestern University, Evanston, IL (US)

( * ) Notice: Subject to any disclaimer, the term of this patent is extended or adjusted under 35 U.S.C. 154(b) by 61 days.

This patent is subject to a terminal disclaimer.

(21) Appl. No.: 14/162,253

(22) Filed: Jan. 23, 2014

(65) Prior Publication Data

US 2014/0206630 A1 Jul. 24, 2014

Related U.S. Application Data

(60) Provisional application No. 61/756,029, filed on Jan. 24, 2013.

(51) Int. Cl.

| | | |
|---|---|---|
| *A61K 31/05* | (2006.01) | |
| *C09D 4/00* | (2006.01) | |
| *A01N 31/16* | (2006.01) | |
| *A01N 43/16* | (2006.01) | |
| *B01D 15/08* | (2006.01) | |
| *C08J 7/06* | (2006.01) | |
| *A61K 31/7028* | (2006.01) | |
| *C02F 1/28* | (2006.01) | |
| *C09D 5/00* | (2006.01) | |
| *C08G 65/44* | (2006.01) | |
| *A61K 31/192* | (2006.01) | |
| *A61K 31/353* | (2006.01) | |
| *A61K 31/7034* | (2006.01) | |
| *C02F 101/20* | (2006.01) | |
| *C02F 101/22* | (2006.01) | |
| *A61K 36/00* | (2006.01) | |

(52) U.S. Cl.
CPC .............. *A61K 31/05* (2013.01); *A01N 31/16* (2013.01); *A01N 43/16* (2013.01); *A61K 31/192* (2013.01); *A61K 31/353* (2013.01); *A61K 31/7028* (2013.01); *A61K 31/7034* (2013.01); *B01D 15/08* (2013.01); *C02F 1/285* (2013.01); *C02F 1/288* (2013.01); *C08G 65/44* (2013.01); *C08J 7/065* (2013.01); *C09D 4/00* (2013.01); *C09D 5/00* (2013.01); *A61K 36/00* (2013.01); *C02F 2101/20* (2013.01); *C02F 2101/22* (2013.01); *C02F 2305/00* (2013.01); *C08J 2369/00* (2013.01)

(58) Field of Classification Search
None
See application file for complete search history.

(56) References Cited

U.S. PATENT DOCUMENTS

| | | | |
|---|---|---|---|
| 3,861,942 A * | 1/1975 | Guestaux | ...................... 430/533 |
| 4,732,817 A | 3/1988 | Lotz et al. | |
| 5,006,383 A * | 4/1991 | Achille | ................... B32B 15/08 |
| | | | 220/62.11 |
| 5,622,848 A * | 4/1997 | Morrow | .................. A23L 1/097 |
| | | | 205/556 |
| 6,027,578 A | 2/2000 | Marzano | |
| 7,976,692 B2 | 7/2011 | Hu et al. | |
| 8,017,050 B2 | 9/2011 | Freeman et al. | |
| 8,541,060 B2 | 9/2013 | Messersmith et al. | |
| 2008/0149566 A1 | 6/2008 | Messersmith et al. | |
| 2009/0074674 A1* | 3/2009 | Katti | ...................... A61K 9/148 |
| | | | 424/9.42 |
| 2010/0068297 A1* | 3/2010 | Naughton | ............... A01N 65/00 |
| | | | 424/630 |
| 2010/0212542 A1 | 8/2010 | Nojima | |

(Continued)

FOREIGN PATENT DOCUMENTS

| | | | | |
|---|---|---|---|---|
| CN | 101756278 A * | 6/2010 | ............. A23L 15/00 |
| CN | 102020779 A * | 4/2011 | ............. B65D 65/46 |

(Continued)

OTHER PUBLICATIONS

Seung et al., KR 827530, 2008, Abstractor translation. Retreived on Aug. 10, 2015 from Derwent Innovations Index.*
Kim et al., KR 2003094968, 2003, Abstractor translation. Retreived on Aug. 10, 2015 from Derwent Innovations Index.*
Nury, FR 2731876, 1996, Abstractor translation. Retreived on Aug. 10, 2015 from Derwent Innovations Index.*

(Continued)

*Primary Examiner* — Shaojia A Jiang
*Assistant Examiner* — Dale R Miller
(74) *Attorney, Agent, or Firm* — Quales and Brady, LLP

(57) ABSTRACT

A method of making a facile, surface-independent, polyphenol coating is disclosed. In general, the method includes contacting at least a portion of the substrate to be coated with an aqueous solution containing one or more salts and one or more nitrogen-free phenolic compounds. Substrates of all kinds may be used, and compounds used to make the coating may include epigallocatechin-3-gallate (EGCG), epigallocatechin (EGC) and epicatechin-3-gallate (ECG), tannic acid, gallic acid, pyrogallol, and/or other nitrogen-free phenolic compounds. The coating made using the method, methods of using the coating, and kits comprising the coating precursors are also disclosed.

13 Claims, 33 Drawing Sheets

(56) References Cited

U.S. PATENT DOCUMENTS

2011/0110723 A1* 5/2011 Varma et al. ............ 405/128.75
2012/0321566 A1* 12/2012 Liu et al. ........................ 424/48

FOREIGN PATENT DOCUMENTS

DE 3835400 A1 3/1990
JP 58082791 A * 5/1983

OTHER PUBLICATIONS

Del Rio, D., Stewart, A. J., Mullen, W., Burns, J., Lean, M. E., Brighenti, F., & Crozier, A. (2004). HPLC-MSn analysis of phenolic compounds and purine alkaloids in green and black tea. Journal of Agricultural and Food Chemistry, 52(10), 2807-2815.*

Kameda et al. JP 2010/242072, Derwent record, retrieved on Feb. 12, 2016.*

Definition of "saline" in www.freeonlinedictionary.com/saline, reproduced from American Heritage Dictionary, 2011, retrieived on Mar. 7, 2016.*

Sato et al., JP 58082791 A, May 1983, Derwent record, Retreived on Jul. 11, 2016 from Thompson Reuters.*

Vermerris, W and Nicholson, R. Phenolic Compound Biochemistry. Springer Verlag, 2008. ISBN: 978-1-4020-5163-0.*

Sato et al., JP 58082791 A, 1983, human translation of Embodiment 2. Received from Steven Spar certified japanese translator in USPTO STIC on Jan. 10, 2017.*

Database WPI, Thomson Scientific, XP-002726701 (JP2000136325), XP-002726702 (JPH05112740), XP-002726703 (JPH0565433), cited in PCT/US2014/012725 International Search Report dated Jul. 21, 2014.

PCT International Search Report and Written Opinion, PCT/US2014/012725, dated Jul. 21, 2014.

Chen, X., Beutler, J.A., McCloud, T.G., Loehflem, A. Yang, L., Dong, H.F., . . . & Howard, O.Z. (2003). Tannic Acid is an Inhibitor of CXCL12 (SDF-1α)/CXCR4 with Antiangiogenic Activity. Clinical Cancer Research, 9(8), 3115-3123.

Kim, T.J., Silva, J.L., Kim, M.K., & Jung, Y.S. (2010). Enhanced Antioxidant Capacity and Antimicrobial Activity of Tannic Acid by Thermal Processing. Food Chemistry, 18(3), 740-746.

* cited by examiner

Figure 2A-D

A:
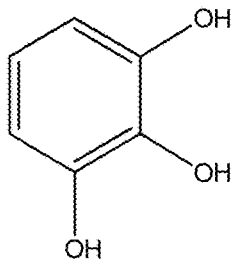
B:
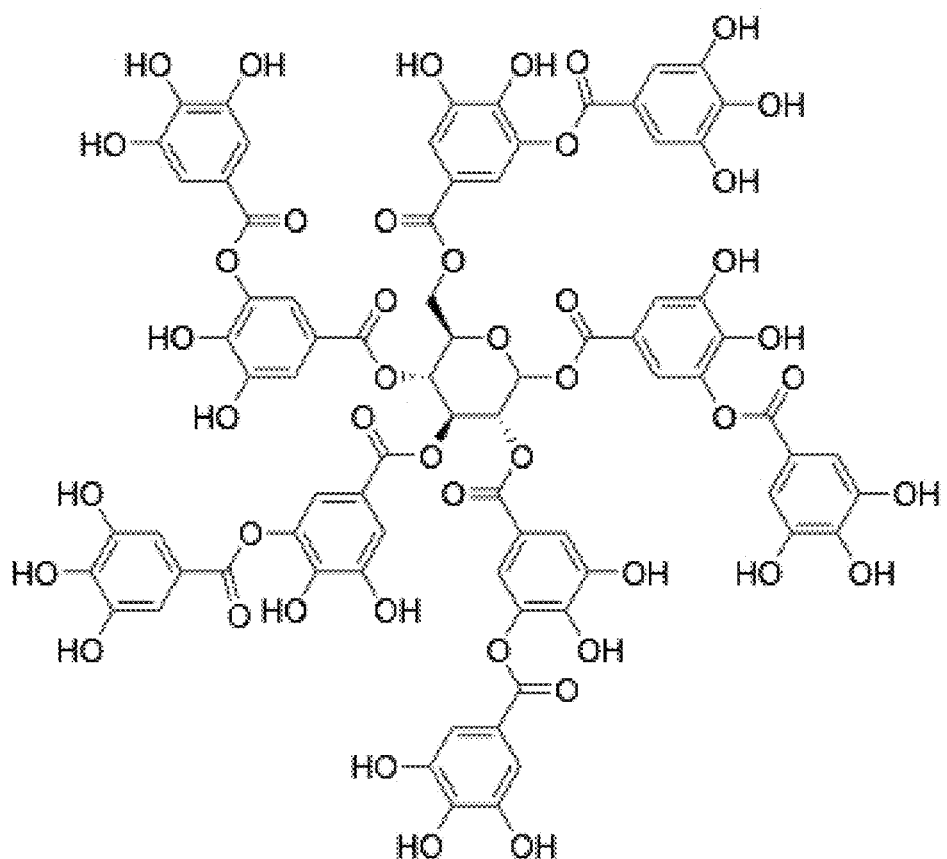
Figure 4A-B

PHENOLIC COATINGS AND METHODS OF MAKING AND USING SAME

STATEMENT REGARDING FEDERALLY-SPONSORED RESEARCH OR DEVELOPMENT

This invention was made with government support under Grant Number R37 DE 014193 awarded by the National Institutes of Health. The government has certain rights in the invention.

CROSS-REFERENCE TO RELATED APPLICATIONS

This application claims the benefit of U.S. Provisional Patent Application No. 61/756,029 filed on Jan. 24, 2013, which is incorporated by reference herein in its entirety for all purposes.

NAMES OF PARTIES TO A JOINT RESEARCH AGREEMENT

The claimed invention was made as a result of activities undertaken within the scope of a joint research agreement between Baxter Healthcare Corporation and Northwestern University.

FIELD OF THE INVENTION

This invention is directed to polymeric coatings that are spontaneously deposited on a substrate surface when the substrate surface is contacted with an aqueous solution comprising an effective amount of one or more nitrogen-free phenolic compounds.

BACKGROUND OF THE INVENTION

Modification of material surfaces plays a central role in modern chemical, biological and material sciences, as well as in applied sciences, engineering and technology. Methods for the modification of bulk material substrates have been developed by interfacial chemistry using organothiol-metals, enediol-oxides, silane-oxides, and other physicochemical methods, in which the predominant purpose is to impose desired properties on non-functional substrates. Molecules utilized for surface modification mostly have bifunctional end groups in which one end anchors to substrates and the other end provides chemical functionality to the substrate surface.

The existing toolbox for functional modification of material/substrate surfaces includes methods such as self-assembled monolayer (SAM) formation, functionalized silanes, Langmuir-Blodgett deposition, layer-by-layer assembly, and genetically-engineered surface-binding peptides. Although widely implemented in research, these conventional methods have limitations for widespread practical use. For instance, chemical specificity between interfacial modifiers and substrates (e.g., alkanethiols on noble metals and silanes on oxides) and complex instrumentation are typically required. In addition, the substrate size/shape (Langmuir-Blodgett deposition) is often limited, or multi-step procedures for implementation (layer-by-layer assembly and surface-binding genetically engineered peptides) are required. Further, existing compounds are often expensive and/or difficult to use.

Methods comprising the single-step coating of substrates with active agents are known in the art. For example, dopamine is capable of spontaneously modifying a variety of substrate surfaces under oxidative conditions (see U.S. Pat. No. 8,541,060 to Messersmith et al.). Dopamine contains a primary amine that facilitates intramolecular cyclization to form the 5,6-dihydroxyindole intermediate that is essential for polydopamine formation. Thus, one of skill in the art would have no reasonable expectation that the method disclosed in the '060 patent would be successful using a nitrogen-free surface modifying agent. Furthermore, polydopamine coatings as described in '060, related patents, and in the academic literature are, without exception, dark colored coatings, as they are closely related to the chemical composition of melanin pigments. The dark color conferred by polydopamine coatings is problematic for many practical applications of the technology where masking or discoloration of the inherent substrate appearance is to be avoided for aesthetic or performance reasons.

In addition, coatings derived from natural sources are also known to the art. For example, tannic acid has been used to modify substrate surfaces (see Caruso et al. 2013). The Caruso art requires the use of trivalent metal ions ($Fe^{3+}$, $V^{3+}$, $Gd^{3+}$, or $Cr^{3+}$ ions) and relies on metal-oxygen coordination bonds formed between the tannic acid and trivalent metal ions for formation of the coating. They show that their coatings do not form in the absence of trivalent metal ions. Additionally, these coordination-based coatings require an acidic-to-basic pH adjustment to form. Furthermore, the Caruso art produces coatings that are darkly colored and are inherently unstable at pH values less than 7.0. Moreover, the coatings based on Caruso art utilize high concentrations of iron, which will likely be toxic to biological systems if biomedical applications are pursued. Coatings that incorporate tannic acid as one component of a multi-component coating have been formed by so-called layer-by-layer technology (see Shutava et al. 2005). However, layer-by-layer coatings involve multi-step deposition processes and require the use of other molecules for formation. In contrast, the present invention describes a general method requiring only a plant-based or plant-inspired phenol or polyphenol precursor compound deposited in a single step to yield colorless coatings that are stable over a wide range of pH conditions.

Accordingly, cost-effective and easy-to-use compounds and methods for the surface-independent modification of a substrate whereby specific functional moieties can be displayed on the surface are needed.

BRIEF SUMMARY OF THE INVENTION

The inventors demonstrate herein that nitrogen-free phenolic compounds can be used to form macromolecular coatings on both nonporous and porous solid substrates. Specifically, under high ionic strength (saline) conditions in the presence of atmospheric oxygen, aqueous solutions of nitrogen-free phenolic compounds form coatings on immersed substrates. The resultant thin film coatings can be deposited in a single step onto a wide range of materials of variable composition (e.g., organic and inorganic, including gold, steel, silicone rubber, and Teflon®) and surface wettability (both hydrophilic and hydrophobic). A wide range of nitrogen-free phenolic compounds can be used as coating precursors, including without limitation natural polyphenols extracted from plant tissue and synthetic phenolics.

The resulting coatings induce little or no discoloration of the underlying substrate and display intrinsic properties of great practical significance. These include inherent contactand solution-based antibacterial properties. The coatings of the invention also have inherent antioxidant properties, and we demonstrate their use in metal removal from solvents. Furthermore, the coatings of the invention are easily functionalized at the macro-, micro-, and nano-scales, facilitating a variety of additional practical uses. For example, the innate ability of polyphenols to sequester and precipitate polypeptides and proteins can be exploited in these coatings for the purpose of immobilizing biological and synthetic molecules containing nucleophilic sites, such as primary amine or sulfhydryl functionalities. Successful incorporation of antifouling polymers onto pyrogallol-coated surfaces can be achieved for inhibiting biofouling and through the incorporation of hydrophobic molecules, super-hydrophobic surfaces can be designed.

In another example, the high reduction/oxidation (redox) potential of the coatings of the invention permits electroless metallization of noble metals such as silver through simple immersion of coated substrates into silver salt solutions. Deposition of the coatings of the invention onto nanoparticles can be utilized for tuning of bulk and surface properties of nanoparticles, as we show by tuning the longitudinal plasmon resonance of gold nanorods to preferred wavelengths by deposition of the coating followed by controlled electroless metallization of silver shells of variable thickness.

Uniting the ability to deposit onto many types of substrates, remarkable versatility in functional properties and little or no discoloration of the substrate, the coatings of the invention represent a promising technology for use in a variety of consumer, industrial, military and biomedical applications.

In a first aspect, the invention encompasses a method of forming a coating on a substrate surface. The method includes the step of contacting at least a portion of the substrate surface with an aqueous solution that includes an effective amount of one or more natural or synthetic nitrogen-free phenolic compounds, whereby a coating forms on the substrate surface. In some embodiments, the solution may be a saline solution.

In some embodiments, the one or more phenolic compounds may include polyphenols, such as epigallocatechin-3-gallate (EGCG), epigallocatechin (EGC), epicatechin gallate (ECG), or tannic acid. In some embodiments, the one or more phenolic compounds may include other compounds, such as gallic acid and pyrogallol. In some embodiments, the one or more polyphenols can optionally be extracted from plant materials, such as green tea or from cacao beans.

In some embodiments, the solution includes NaCl. In some embodiments, the saline solution is basic. In some such embodiments, the pH of the solution is about 7.8.

In some embodiments, the substrate surface is gold, titanium dioxide, silica, polycarbonate, polytetrafluoroethylene, polystyrene, titanium, and/or stainless steel.

Some embodiments include the optional additional step of contacting the resulting coating with a reactive moiety, whereby the reactive moiety reacts with and becomes bound to the coating. In some such embodiments, the reactive moiety includes a nucleophile or a metal ion. Optionally, the metal ion can be silver ion.

In some embodiments, the reactive moiety comprises silver ion ($Ag^+$), and elemental silver becomes bound to the coating. Optionally, some such embodiments further include the step of contacting the resulting coating with an alkanethiol, whereby the coating becomes superhydrophobic.

In some embodiments, the nucleophile is comprised of a protein or an amine- or thiol-functionalized polymer, including, for example, poly(ethylene glycol) (PEG).

The presence of the amine moiety in dopamine allows for cyclization under oxidative conditions (creating the critical dihydroxyindole structure), yielding enhanced reactivity allowing for further oligomerization and polymerization. Such intuition cannot be translated to phenolic coatings based on absence of amines. Precluded by its melanin-like nature, polydopamine coatings cannot be engineer to afford colorless surface modifications. Phenolic coatings, though, can be tuned to derive a completely colorless material. The phenolic coatings of the present invention also exhibit contact-based antioxidant, antibacterial, antifungal, and anti-inflammatory properties, which are not observed using polydopamine coatings. Additionally, phenolic coatings can be tuned to reduce water contact angles into the superhydrophilic regime (less than 10°), a property that can never be achieved using polydopamine coatings, which display contact angles of approximately 50°.

In a second aspect, the invention encompasses a coating on a surface substrate that is produced by the methods described above.

In a third aspect, the invention encompasses a method of inhibiting bacterial growth on a substrate. The method includes the step of depositing a coating on a substrate surface according to any of the methods described above, whereby the coated substrate effectively kills bacteria on contact or inhibits bacterial growth.

In a fourth aspect, the invention encompasses a method of reducing the concentration of metal in a liquid. The method includes the step of contacting the liquid with the coating as described above, whereby at least some of the metal ions in the sample are captured by the coating and removed from the liquid.

In some embodiments, the heavy metal cations removed by the method may optionally include silver.

In a fifth aspect, the invention encompasses a kit for coating a substrate surface. The kit includes an effective amount of one or more phenolic compounds, and/or one or more polyphenols, and instructions for use. Optionally, the kit may further include a salt and a buffer. Optionally, the salt is sodium chloride. Optionally, the kit may further include a reactive moiety made up of a nucleophile or a metal ion. The metal ion may optionally be silver.

In a sixth aspect, the invention encompasses a method of forming a coating on a substrate surface. The method includes the step of contacting at least a portion of the substrate surface with an aqueous solution comprising an effective amount of one or more nitrogen-free phenolic compounds, whereby a coating forms on the substrate surface.

In some embodiments, the one or more nitrogen-free phenolic compounds may include pyrogallol (PG), epigallocatechin-3-gallate (EGCG), epigallocatechin (EGC), epicatechin gallate (ECG), tannic acid (TA), hydroxyhydroquinone (HHQ), catechin, morin, quercetin, naringenin, naringin, rutin, phloroglucinol, catechol, resorcinol, hydroquinone, phenol, gallic acid, and/or stereoisomers thereof.

As described above, previously developed tannic acid coatings by Caruso et al. are molecular constructs achieved through chemical coordination between galloyl groups of tannic acid and $Fe^{3+}$ (although $V^{3+}$, $Gd^{3+}$, and $Cr^{3+}$ were also used). Because coordination bonds are labile in acidic conditions, the tannic acid and $Fe^{3+}$ films degrade rapidly in weakly acidic conditions. Also, because coordination bonds are the crucial aspect of Caruso's materials, the absence of trivalent metal ions prevent the formation of any coatings. Further, the actual coatings do not form unless the pH is raised from the initial acidic conditions (acidic due to the $Fe^{3+}$) to pH 7.4-8.0. This change induces the formation of coordination bonds. Further still, Caruso's method provides resulting films that are very dark in appearance.

In contrast, the currently claimed phenolic coating methodology reacts with dissolved oxygen in buffered saline (without the need for a change in pH) to deposit coatings, which appear to contain both covalent C—C bonds and non-covalent interactions (hydrophobic interactions, pi-pi stacking, hydrogen bonds). Our phenolic coatings can be tuned to not degrade under non-neutral conditions, and, unlike Caruso et al coatings, can be made colorless. Moreover, the lack of heavy metal ions in our coatings allows for non-toxic interactions with mammalian cells, an important property when considering medical translation of the technology. To date, Caruso's materials have not been shown to be antioxidant, antimicrobial, and/or anti-inflammatory. Finally, as opposed to the present invention's ability to remove heavy metals from water, the films designed by Caruso can be viewed as a source of heavy metals ($Fe^{3+}$, $V^{3+}$, $Gd^{3+}$, and $Cr^{3+}$).

Although coating deposition occurs in the absence of salts, in some embodiments, the aqueous solution includes an effective amount of one or more salts. By "effective amount" we mean an amount effective to achieve an optimal formation of a coating on the substrate surface, where "optimal" is defined as a desired coating thickness or a desired rate of coating formation. In some embodiments the presence of the salt increases the coating thickness and/or rate of coating formation. Although the mechanism of interaction between phenol or polyphenol coating precursor and salt is not fully understood and likely varies by the identity of the salt, we anticipate in some cases the optimization of thickness and/or rate afforded by addition of salt is due to ionic strength induced intermolecular interactions like charge shielding between molecules, leading to aggregation and deposition of molecules in the form of a coating. The one or more salts may include a sodium salt, a potassium salt, a calcium salt, a magnesium salt, a copper salt, and/or a zinc salt. In some such embodiments, the one or more salts may include NaCl, $NaNO_3$, $Na_2SO_4$, KCl, $K_2SO_4$, $MgCl_2$, $CaCl_2$, $CuCl_2$, and/or $ZnCl_2$.

In some embodiments, no salt addition is necessary to spontaneously deposit a coating. For example, the deposition of pyrogallol coating on nanoparticles was optimally achieved from salt-free solution. However, in other embodiments, at least one of the one or more salts in the aqueous solution is at a concentration of at least 0.001 mM. However, in other embodiments, at least one of the one or more salts in the aqueous solution is at a concentration of at least 10 mM. In some other embodiments, at least one of the one or more salts in the aqueous solution is at a concentration of at least 50 mM. In some embodiments, the salt concentration is optionally between 0 mM and a saturated solution, 0.001 mM and 1 mM, between 1 mM and 1,000 mM, between 10 and 10,000 mM, between 15 and 10,000 mM, between 20 and 10,000 mM, between 30 and 10,000 mM, between 40 and 10,000 mM, between 50 and 10,000 mM, between 10 and 1,000 mM, between 15 and 1,000 mM, between 20 and 1,000 mM, between 30 and 1,000 mM, between 40 and 1,000 mM, or between 50 and 1,000 mM.

In some embodiments, the aqueous solution may further include a buffer.

In some embodiments, the pH of the aqueous solution is between 3.0 and 9.0; more preferably, the pH of the aqueous solution is between 6.0 and 9.0.

Some embodiments further include the step of contacting the resulting coating with a reactive moiety, whereby the reactive moiety reacts with and becomes bound to the coating. Optionally, the reactive moiety may include a nucleophile or a metal ion. Exemplary metal ions that could be used include, without limitation, silver ion. Exemplary nucleophiles include, without limitation, biomolecules such as proteins or oligonucleotides, and amine- or thiol-functionalized polymers such as amino- or thiol-terminated poly(ethylene glycol) (PEG).

Some embodiments further include the step of contacting the resulting coating with an alkanethiol, whereby the coating becomes superhydrophobic.

In a seventh aspect, the invention encompasses a coating on a substrate surface as produced by the method described above (as a sixth aspect).

In an eighth aspect, the invention encompasses a method of inhibiting bacterial growth on a substrate by depositing an antibacterial coating on a substrate surface according to the method described above (as a sixth aspect), whereby the coated substrate effectively kills bacteria on contact or inhibits bacterial growth.

In a ninth aspect, the invention encompasses a method of conferring antioxidant properties on a substrate by depositing an antioxidant coating on a substrate surface according to the method described above (as a sixth aspect), whereby the coated substrate has antioxidant activity.

In a tenth aspect, the invention encompasses a method of reducing inflammation caused by contact of cells or tissues with a substrate by depositing an anti-inflammatory coating on a substrate surface according to the method described above (as a sixth aspect), whereby the coated substrate has anti-inflammatory activity.

In an eleventh aspect, the invention encompasses a method of removing metal ions from a liquid. The method includes the step of contacting the liquid with the coating described above (as a seventh aspect), whereby at least some of the metal ions in the liquid are captured by the coating and removed from the aqueous sample.

In some embodiments, the metal ions can include silver ions.

In a twelfth aspect, the invention encompasses a kit for coating a substrate surface. The kit includes an effective amount of one or more phenolic compounds; one or more salts; and instructions for use.

In some embodiments, the kit further includes a buffer. In some embodiments, the kit further includes a reactive moiety containing a nucleophile or a metal ion. An exemplary metal ion that could be used is, without limitation, silver ion.

BRIEF DESCRIPTION OF THE DRAWINGS

FIG. 4A. 1,2,3-trihydroxybenzene (pyrogallol, "PG") chemical structure.

FIG. 4B. Idealized chemical structure of tannic acid ("TA"), with a glucose core containing ten gallate units. The idealized TA structure shown is only one of many compounds identified as TA in the art, with the number of gallate units per molecule in a commercial TA sample potentially ranging from 1-15.

DETAILED DESCRIPTION OF THE INVENTION

Figure 1:
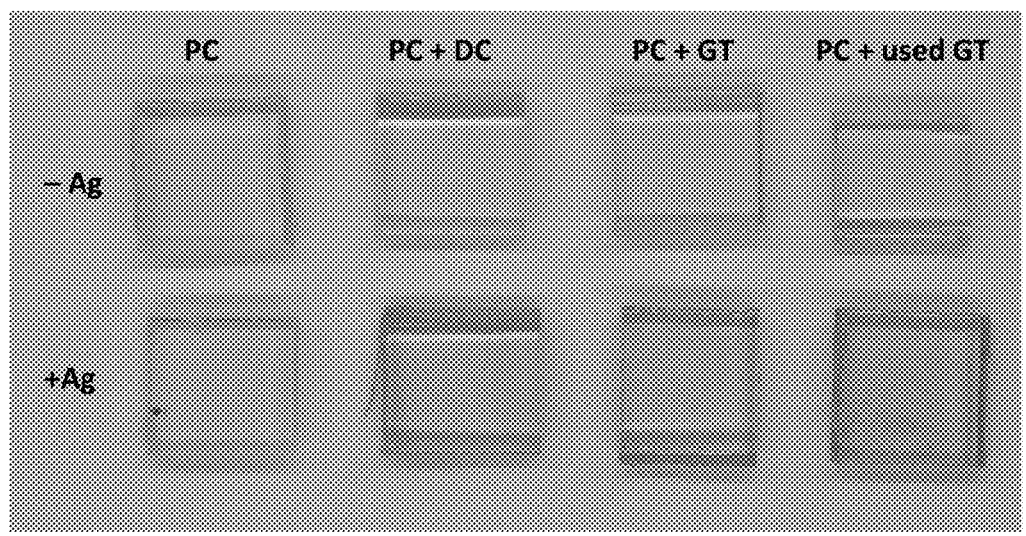
FIG. 1. Color changes associated with modification of polycarbonate (PC) substrates with dark chocolate (DC), green tea (GT) and used green tea (used GT), before (−Ag) and after (+Ag) silver nitrate incubations.

In the specification and in the claims, the terms "including" and "comprising" are open-ended terms and should be interpreted to mean "including, but not limited to . . . ." These terms encompass the more restrictive terms "consisting essentially of" and "consisting of."

As used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The Invention.

The present invention provides a coating formed when an effective amount of an aqueous solution and one or more nitrogen-free phenolic compounds is applied to a portion of a substrate, wherein the substrate surface is coated with and modified by the one or more nitrogen-free phenolic compounds. In one embodiment, the solution may comprise an effective amount of one or more salts sufficient to achieve an optimal coating. Methods of making and using the coating, as well as kits for using the coating, are also provided.

"Phenolic compounds" or "phenols" are nitrogen-free compounds comprising one or more aromatic rings having at least one hydroxyl group attached thereto. The one or more aromatic rings are not limited to having a single hydroxyl group, as in phenol, but may each include more than one hydroxyl group, as in a catechol.

Polyphenols are a structural class of nitrogen-free compounds characterized by the presence of two or more phenolic structural units, and may include any number of natural or synthetic precursors that yield coatings. The "polyphenols" of the present invention are nitrogen-free and may be considered either "phenols" or "polyphenols" according to the widely accepted definitions known to one of skill in the art. Although the chemical "phenol" itself has only one phenolic hydroxyl group on the aromatic ring, a "phenolic structural unit" may include two or more hydroxyl groups on the same aromatic ring. For example, catechol and resorcinol, which include two hydroxyl groups on the same aromatic ring, and pyrogallol and phloroglucinol, which have three hydroxyl groups on the same aromatic ring, are considered to have a "phenolic structural unit." Polyphenols and phenolic structural units may have oxygen-based substituents other than hydroxyl groups; as might be expected, ether and ester linkages are common, as are various carboxylic acid derivatives.

Polyphenols are known to modulate gene expression and have been used in the treatment of cancer. In addition, polyphenols have antioxidant activity against reactive oxygen species (ROS), which are involved in immune responses.

The coatings of the invention can be deposited on a substrate surface as a thin (i.e., a monolayer ranging from about 0.5 to about 50 nm or more) coating on virtually any material. Compared to other compounds used to coat substrates, polyphenols formed from the nitrogen-free phenolic compounds have the advantage of being inexpensive, adherent, and simple to deposit onto substrates without the need for surface pre-treatment. Polyphenol nanolayers can form on virtually any material surface, including noble metals, oxides, semiconductors, ceramics, synthetic polymers, and graphene oxide, as well as on superhydrophobic surfaces.

Polyphenols are found in virtually all families of plants, and can comprise up to 50% of the dry weight of plant tissue. Polyphenols can be derived naturally (i.e., by extracting them from plants) or synthetically. By "plant polyphenols", we mean polyphenols derived from plant tissues, such as, for example and without limitation, tea leaves, cacao/chocolate, grapes/red wine, etc. In some embodiments, the plant polyphenols used in the present invention include epigallocatechin-3-gallate (EGCG), epigallocatechin (EGC) and epicatechin gallate (ECG), and tannic acid. Tannic acid ("TA"), as is widely understood in the art, includes without limitation a number of compounds containing from 1-15 gallic acids bound together with ester linkages surrounding a glucose core. Commercial TA typically consists of a mixture of tannic acid molecules of variable molecular weight. Pentagalloyl glucose fits the definition of commercial tannic acid and is, therefore, embodied within the present invention. The coating precursor embodied within this invention includes both purified compounds as well as mixtures of multiple compounds derived from plant tissue as is found in commercial TA sources. Other nitrogen-free phenolic compounds, such as gallic acid and pyrogallol, can also be used in the present invention.

By "tea", we mean any tea leaf containing an effective amount of polyphenols. In some embodiments, the tea may be green tea, white tea, red tea, oolong tea, black tea and more.

By "cacao" we mean any cacao plant tissue containing an effective amount of polyphenols. For instance, this includes cacao bean, which contains a high concentration of polyphenol. Additionally, cacao liquor is a major component of chocolate, and includes an effective amount of polyphenol. By "effective amount" we mean an amount of polyphenol sufficient to achieve the optimal coating in the present invention. In some embodiments, the polyphenol may be derived from chocolate, such as dark chocolate having at least 80-90% cacao.

By "tannic acid" we mean a specific form of tannin, a type of polyphenol. Commercial tannic acid is usually extracted from Tara pods, gallnuts or Sicilian Sumac leaves and is typically a mixture of many compounds as described above, any one of which, or any combination of which, can be used to achieve the coatings described in this invention.

By "gallic acid" we mean the crystalline organic acid found in gallnuts, sumach, tea leaves, oak bark, and many other plants, or synthesized chemically, both in its free state and as part of tannic acid and other hydrolyzable tannins. Gallic acid is obtained by the hydrolysis of tannic acid. When heated above 220° C., gallic acid loses carbon dioxide to form pyrogallol, or 1,2,3-trihydroxybenzene, $C_6H_3(OH)_3$.

By "pyrogallol" we mean 1,2,3-trihydroxybenzene, $C_6H_3(OH)_3$. Pyrogallol can be produced from gallic acid as noted above and can also be extracted from the aquatic plant *Myriophyllum spicatum*.

Plant-Derived Polyphenol Coatings.

In one embodiment, the invention comprises a coating formed when a saline solution comprising one or more nitrogen-free phenolic compounds is applied to a portion of a substrate, wherein the substrate surface is coated. In some embodiments, the phenolic compounds are derived from a plant derived extract that may include plant polyphenols, such as epigallocatechin-3-gallate (EGCG), epigallocatechin (EGC) and epicatechin gallate (ECG), and tannic acid. Other plant derived nitrogen free phenolic compounds, including without limitation gallic acid and pyrogallol, can be used.

The coating may also comprise a reactive moiety, wherein the reactive moiety reacts with and is bound to the coated surface of the substrate. The reactive moiety may comprise a nucleophile or a metal ion, such as silver ion. In some embodiments, a metal salt, such as NaCl, is added to enhance the coating.

By "effective amount" we mean an amount sufficient that, when contacted with a substrate surface under reactive conditions, is sufficient to effect the expected reaction. In one embodiment, we mean an amount sufficient to deposit a coating on the substrate.

By "coating" we mean depositing a macromolecular coating on the substrate surface. The thickness of the coating may vary according to the needs of the user and the surface to be treated. Using techniques known to one of skill in the art, these variables can be addressed without undue experimentation.

By "applied" we mean any method of coating a surface known to the art, including spin-coating, painting, dipping, washing, spraying, brushing, and the like.

By "substrate" we mean any material known to the art, including a surface formed from polycarbonate (PC), polysulfone (PS), polyisoprene (PI), polytetrafluoroethylene (PTFE), silicone rubber (SiR), titanium dioxide ($TiO_2$), gold (Au), and aluminum oxide ($Al_2O_3$). In other embodiments, the substrate may be any surface formed from polyurethane and its copolymers, silicone and its copolymers, ethylene vinyl-acetate, thermoplastic elastomers, polyvinyl chloride, polyolefins, cellulosics, polyamides, polytetrafluoroethylenes, polyesters, polycarbonates, polysulfones, and acrylonitrile butadiene styrene copolymers; acrylics; metals and alloys based on titanium, stainless steel, nickel-chrome, nitinol or cobalt-chrome; ceramics of alumina and glass-ceramics and the like. For instance, the surface can comprise a metallic material or an alloy such as, but not limited to, cobalt, nickel, chromium, molybdenum, stainless steel (316L), high nitrogen stainless steel, cobalt chrome, tantalum, nickel-titanium alloy, platinum-iridium alloy, gold, magnesium, or combinations thereof. Surfaces comprising bioabsorbable or biostable polymers could also be used with the embodiments of the present invention.

The substrate may be without limitation a nonporous, porous, membranous or fibrous substrate of any geometry.

The substrate may be a medical device or any part of a medical device that comes in contact with a patient, including but not limited to self-expandable stents, balloon-expandable stents, stent-grafts, grafts (e.g., aortic grafts), vascular grafts, artificial heart valves, cerebrospinal fluid shunts, pacemaker electrodes, guide wires, ventricular assist devices, artificial hearts, cardiopulmonary by-pass pumps and circuits, blood oxygenators, endocardial leads, catheters, implantable vascular access ports, blood storage bags, vascular stents, blood tubing, central venous catheters, arterial catheters, vascular grafts, intraaortic balloon pumps, heart valves, cardiovascular sutures, total artificial heart and ventricular assist pumps, blood oxygenators, blood filters, hemodialysis units, hemoperfusion units, plasmapheresis units, and hybrid artificial organs such as pancreas or liver and artificial lungs and the like.

In alternate embodiments, the invention comprises a method of modifying a substrate surface comprising contacting at least a portion of the substrate with a solution containing an effective amount of plant-derived polyphenol, wherein the substrate surface is modified. The method may also comprise contacting the surface-modified substrate with a reactive moiety, wherein the reactive moiety reacts with and is bound to the modified surface.

Methods of Use.

The coating and methods of the present invention will be useful in important fields including biocompatible coatings of medical devices, surface modifications of drug delivery carriers and tissue engineering scaffolds, biosensors, biofouling-resistant, industrial and consumer coatings, semiconductors, metal removal, control of wetting properties of solid or porous objects, application of catalysts to surfaces, and fabrication of next generation electronic displays.

Kits.

In an alternate embodiment of the invention, a kit for preparing and using the novel macromolecular coating of the present invention is provided. In one embodiment, the kit comprises a nitrogen-free phenolic compound according to the present invention and instructions for use.

By "instructions for use" we mean a publication, a recording, a diagram, or any other medium of expression which is used to communicate the usefulness of the invention for one of the purposes set forth herein. The instructional material of the kit can, for example, be affixed to a container which contains the present invention or be shipped together with a container which contains the invention. Alternatively, the instructional material can be shipped separately from the container or provided on an electronically accessible form on an internet website with the intention that the instructional material and the plant-derived polyphenol coating be used cooperatively by the recipient.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed description of the present invention is to be regarded as illustrative in nature and not restrictive.

THE EXAMPLES

The following examples are, of course, offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

Example 1

Surface Modification Through Polyphenols from Green Tea and Dark Chocolate Extracts Under Mildly-Basic, Saline, Aqueous Conditions Crude extracts of green tea (GT) and dark chocolate (DC) were prepared from raw food products (Table 1) using methods known to the art. The resultant extracts, in solutions buffered at pH 7.8 with 100 mM bicine, further supplemented with 600 mM NaCl, resulted in adherent coating depositions on polycarbonate substrates following 4 h exposure at room temperature with mild agitation. The resultant coatings were confirmed through X-ray photoelectron spectroscopy, as seen by altered carbon-to-oxygen (C/O) ratios. Additionally, the resultant materials, once exposed to 100 mM $AgNO_3$ for 24 h, were able to metallize silver.

TABLE 1

Elemental composition of polycarbonate (PC) modified with dark chocolate (DC), green tea (GT), and used green tea (used GT) extract, followed by incubation in silver nitrate (Ag), as determined by XPS.

| Surface | Elemental Composition | | | |
|---|---|---|---|---|
|  | C | O | N | Ag |
| PC | 85.3% | 14.7% | 0.0% | 0.0% |
| + Ag | 84.8% | 14.9% | 0.0% | 0.4% |
| PC + DC | 80.6% | 17.8% | 1.6% | 0.0% |
| + Ag | 72.0% | 19.3% | 1.4% | 7.3% |
| PC + GT | 76.8% | 22.4% | 0.7% | 0.0% |
| + Ag | 77.3% | 18.1% | 1.0% | 3.6% |
| PC + used GT | 74.1% | 25.4% | 0.6% | 0.0% |
| + Ag | 71.7% | 22.9% | 0.7% | 4.7% |

Aside from XPS analysis, the emergence of a dark amber color was associated with metallization of silver onto polycarbonate substrates coated with the polyphenol extracts of the present invention (FIG. 1). The redox properties of the polyphenol coatings were attributed to the presence of polyphenols, which, in solution, exhibits reductive properties towards silver nitrate salts.

Extractions of polyphenol from raw foods were performed as follows: Green tea leaves were combined with 70% methanol in water at a concentration of 1 g tea leaves per 10 mL solvent. The tea leaves were sonicated for 10 minutes, followed by centrifugation at 1,000×g for 10 minutes. The supernatant was saved and the tea leaves were re-subjected to the same extraction protocol for 2 additional times. Combined supernatants were concentrated under reduced pressure, filtered through a 0.22 μm filter, and the resultant fraction frozen and lyophilized prior to use.

Dark chocolate (90% cacao content) was defatted by sonication of 1 g per 10 mL of hexane for 10 minutes, followed by centrifugation at 1,000×g for 10 minute. The defatting protocol was repeated once more. The defatted chocolate was suspended in 70% acetone and 0.2% acetic acid in water at a concentration of 1 g chocolate per 10 mL solvent. The chocolate was sonicated for 10 minutes, followed by centrifugation at 1,000×g for 10 minutes. The supernatant was saved and the chocolate was re-subjected to the same extraction protocol for 2 additional times. Combined supernatants were concentrated under reduced pressure, filtered through a 0.22 μm filter, and the resultant fraction frozen and lyophilized prior to use.

Used green tea was obtained after brewing a cup of green tea for 10 minutes. The remaining green tea leaves were removed from the brewed liquid and combined with 0.12 M HCl at a concentration of 1 g tea leaves per 10 mL solvent. The tea leaves were sonicated for 10 minutes, followed by centrifugation at 1,000×g for 10 minutes. The supernatant was filtered through a 0.22 μm filter, frozen and lyophilized prior to use.

Figure 2:
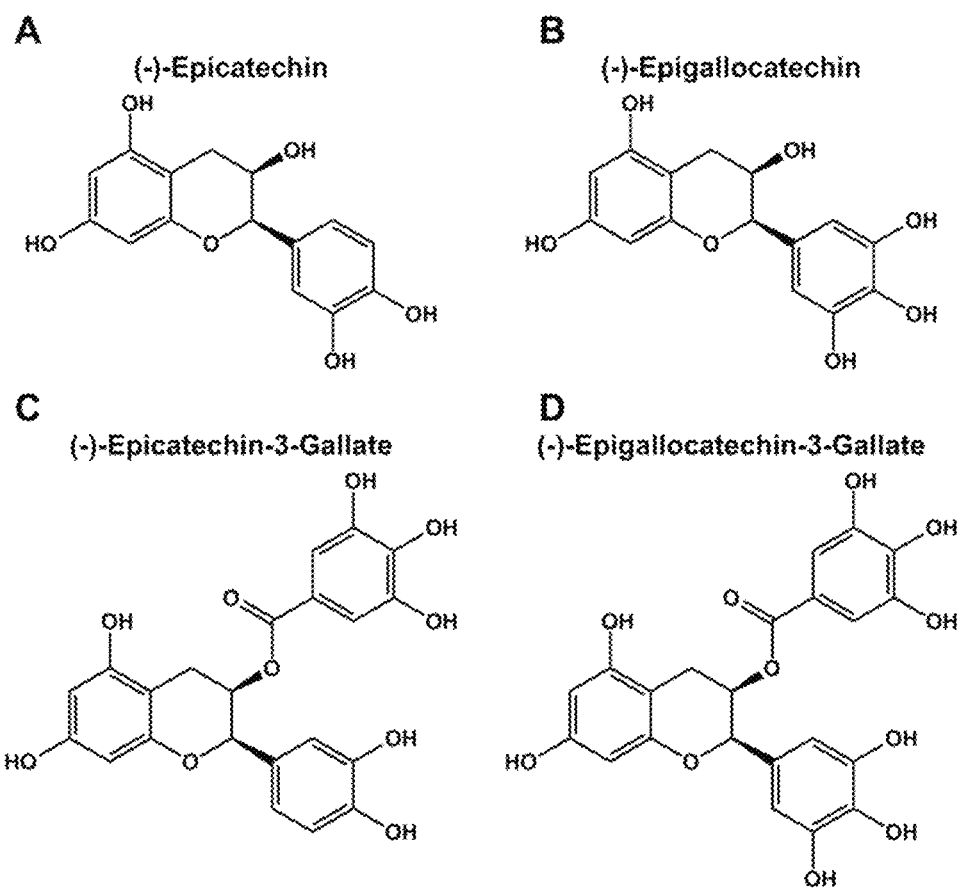
FIG. 2A. Chemical structures of naturally-occurring EC found in green tea and chocolate.
FIG. 2B. Chemical structures of naturally-occurring EGC found in green tea and chocolate.
FIG. 2C. Chemical structures of naturally-occurring ECG found in green tea and chocolate.
FIG. 2D. Chemical structures of naturally-occurring EGCC found in green tea and chocolate.
Figure 3:
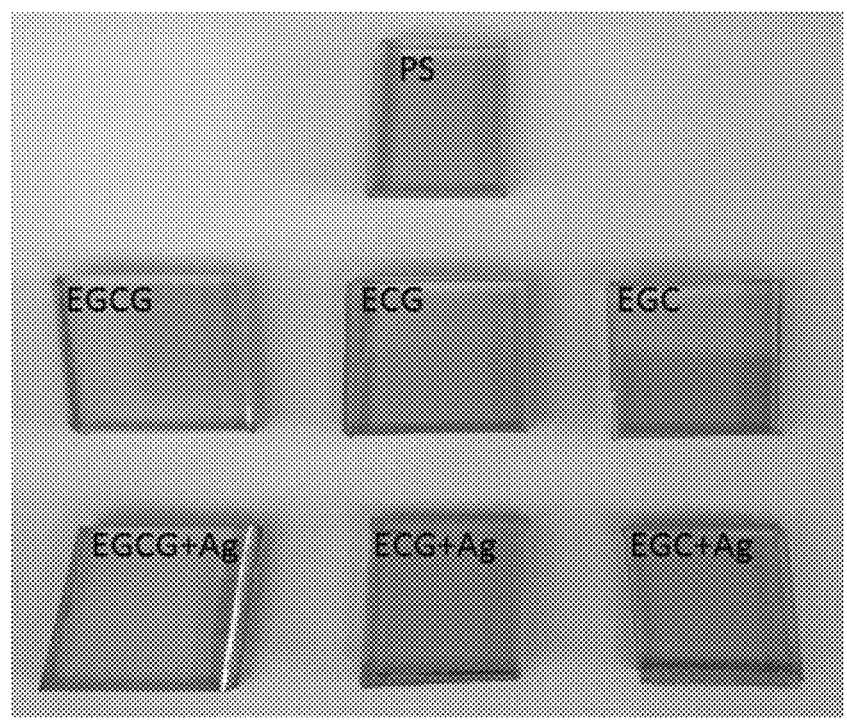
FIG. 3. Color changes associated with the deposition of coatings derived from naturally-occurring green tea and chocolate phenols or polyphenols on polysulfone (PS), before and after metallization of silver.

Given the prevalence of various trihydroxybenzene-substituted polyphenol molecules, such as epigallocatechin-3-gallate (EGCG), epigallocatechin (EGC) and epicatechin gallate (ECG), previously identified in green tea and dark chocolate, specific purified compounds were utilized to deposit polyphenol-based coatings (FIG. 2). Qualitative observations of surface modified with EGCG, EGC and ECG, following metallization in silver nitrate solution, indicated that coatings are deposited as expected (FIG. 3).

Example 2

Pyrogallol Coating Deposition Under Mildly-basic, Saline, Aqueous Conditions

Pyrogallol (PG, FIG. 4) coating deposition under mildly-basic, saline, aqueous condition was achieved on a variety of substrates. Pyrogallol is a more cost-effective phenolic compound to use and obtain, as compared to many other phenols and polyphenols. The dip coating strategy was performed by incubating the choice substrate in a 0.1 to 2.0 mg/mL solution of pyrogallol, buffered at pH 7.8 with 100 mM bicine, further supplemented with 600 mM NaCl to adjust ionic strength. The incubation was performed at room temperature with mild agitation for duration of 0.5 h to 24 h.

To date, substrates made of the following materials have been successfully modified with Pyrogallol according to the present invention: Polycarbonate (PC), Polysulfone (PS), Polyisoprene (PI), Polytetrafluoroethylene (PTFE), Poly (ether ether ketone) (PEEK), Polystyrene, Silicone rubber (SiR), Titanium dioxide ($TiO_2$), Gold (Au), and Aluminum oxide ($Al_2O_3$). We expect the pyrogallol coating of the present invention to be effective on all substrates.

Figure 5:
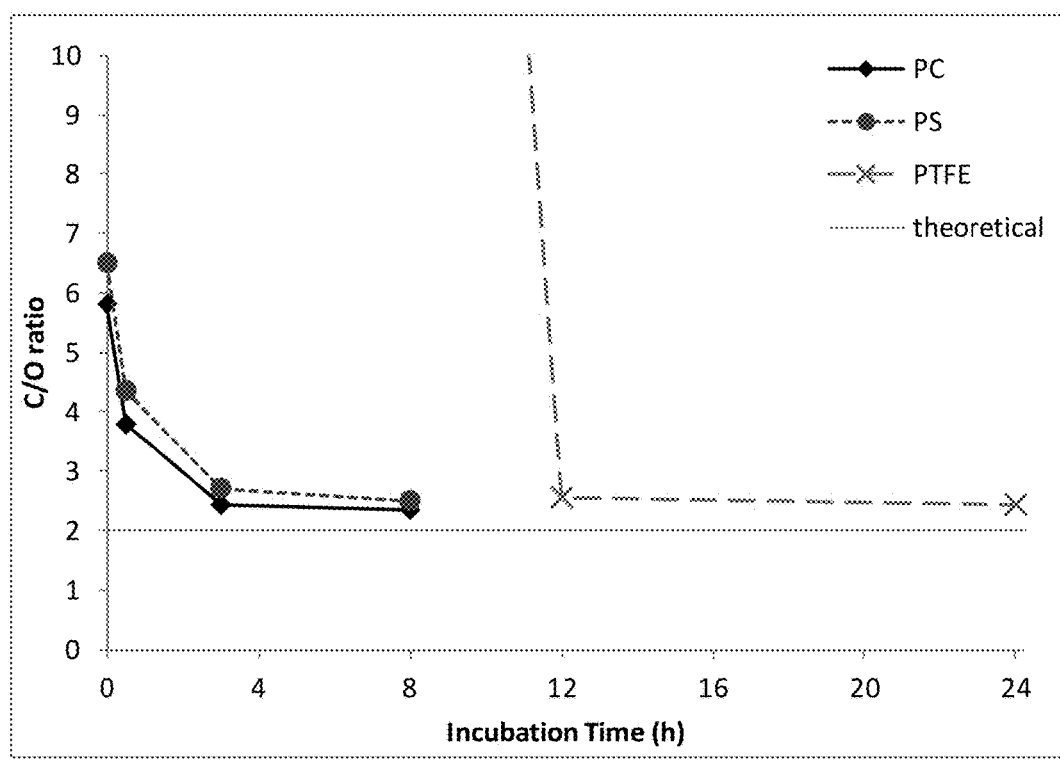
FIG. 5. Carbon-to-oxygen ratios for three substrates (PC, PS & PTFE) modified with pyrogallol, as assessed by XPS.

Modification of the various substrates has been confirmed by X-ray photoelectron spectroscopy (XPS) and contact angle measurement, using water as solvent. XPS data suggests that the theoretical carbon-to-oxygen ration (C/O) of 2:1 is approached after substrates have been incubated with pyrogallol (FIG. 5), and the measured static contact angles readily decreased to approximately 20° after pyrogallol modification.

Figure 6:
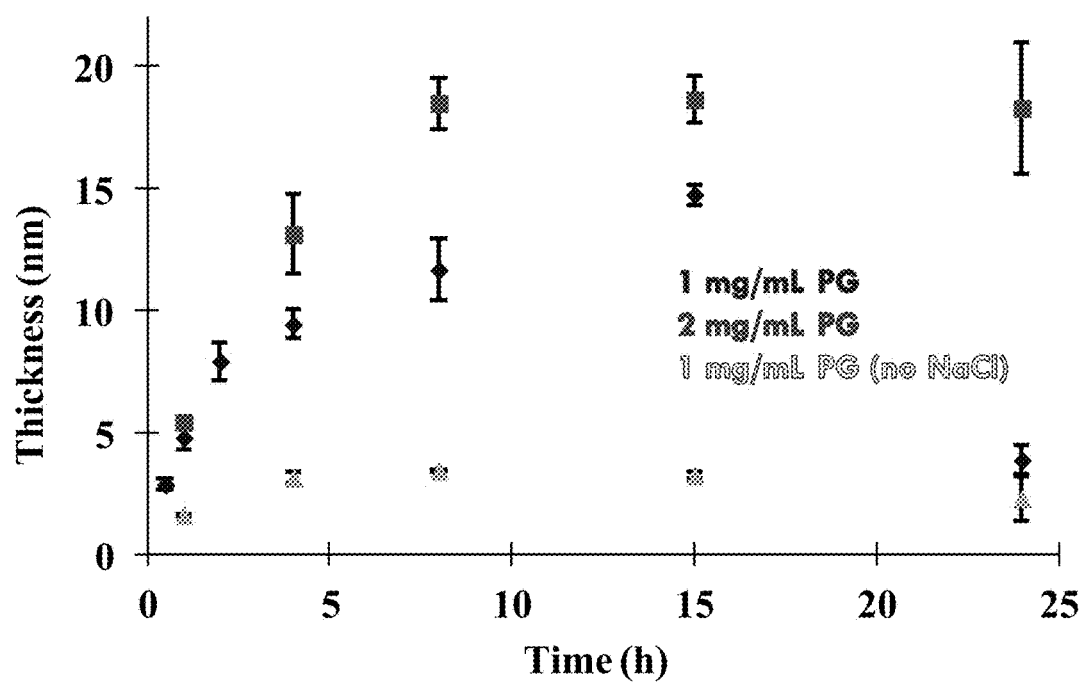
FIG. 6. Pyrogallol (PG) coating thickness growth on gold as a function of time.

Using gold substrates, kinetic studies of coating thickness as a function of pyrogallol concentration, ionic strength adjustment and time have been performed (FIG. 6).

Figure 7:
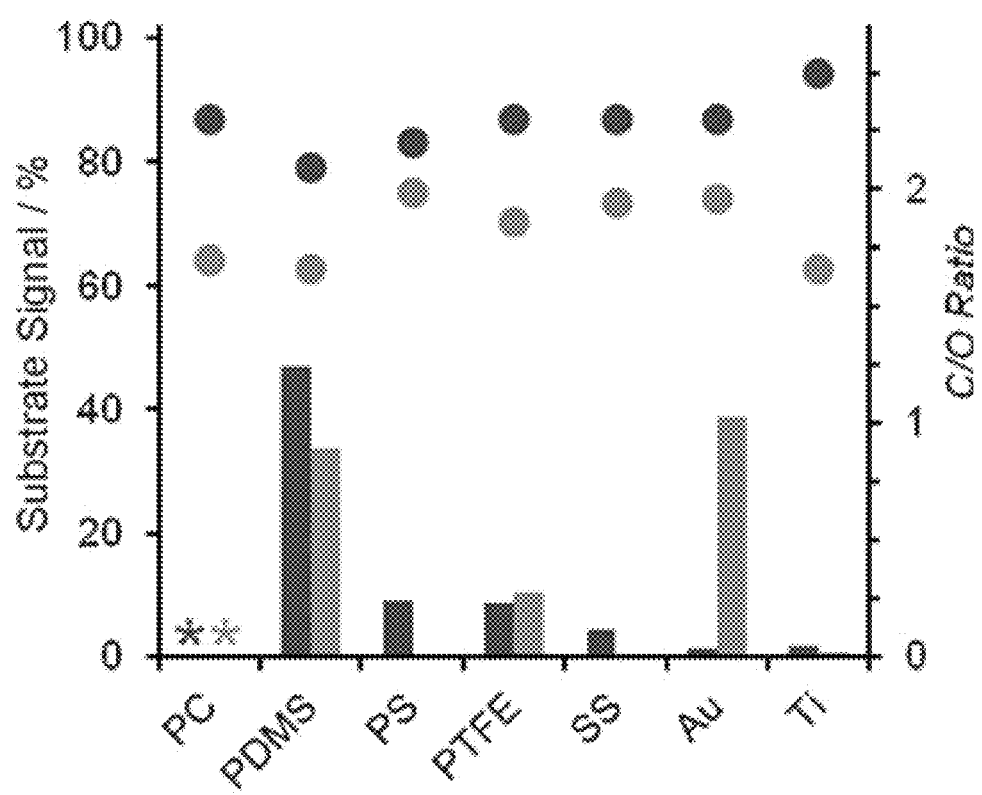
FIG. 7. XPS analysis, including strength of the underlying substrate signal (bars) and carbon-to-oxygen (C/O) ratio (circles), for various materials coated with PG (dark gray) and TA (light gray).

Approximately 18 nm-thick coatings were achieved using 2 mg/mL pyrogallol solutions after 15 h. The use of NaCl-supplementation was found to enhance coating thickness. Additionally, we have found that tannic acid (TA, FIG. 4) can be deposited on a variety of substrates under identical incubation conditions (FIG. 7).

Example 3

Electroless Metallization of Silver on Surfaces via Pyrogallol

Figure 8:
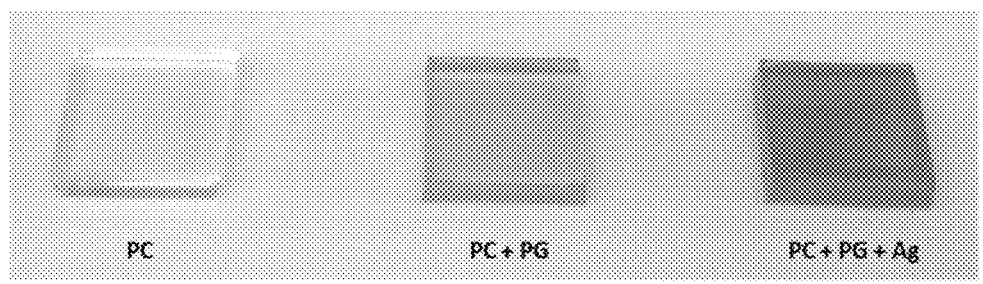
FIG. 8. Color changes associated with the modification of polycarbonate with pyrogallol and, subsequently, silver nitrate.
Figure 9:
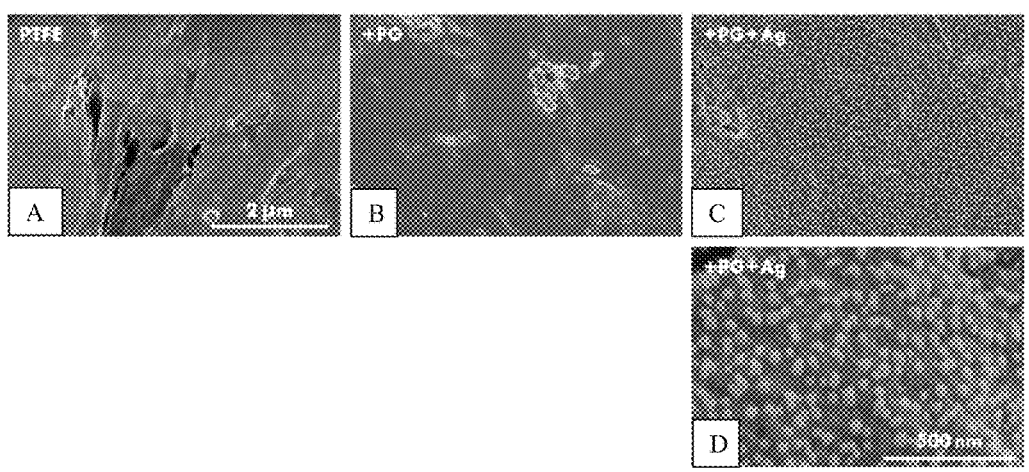
FIG. 9A. Scanning electron micrograph of polytetrafluoroethylene (PTFE).
FIG. 9B. Scanning electron micrograph of PTFE modified with PG.
FIG. 9C. Scanning electron micrograph of PTFE modified with PG and silver nitrate.
FIG. 9D. Scanning electron micrograph of PTFE modified with pyrogallol and silver nitrate shown at a higher magnification.
Figure 10:
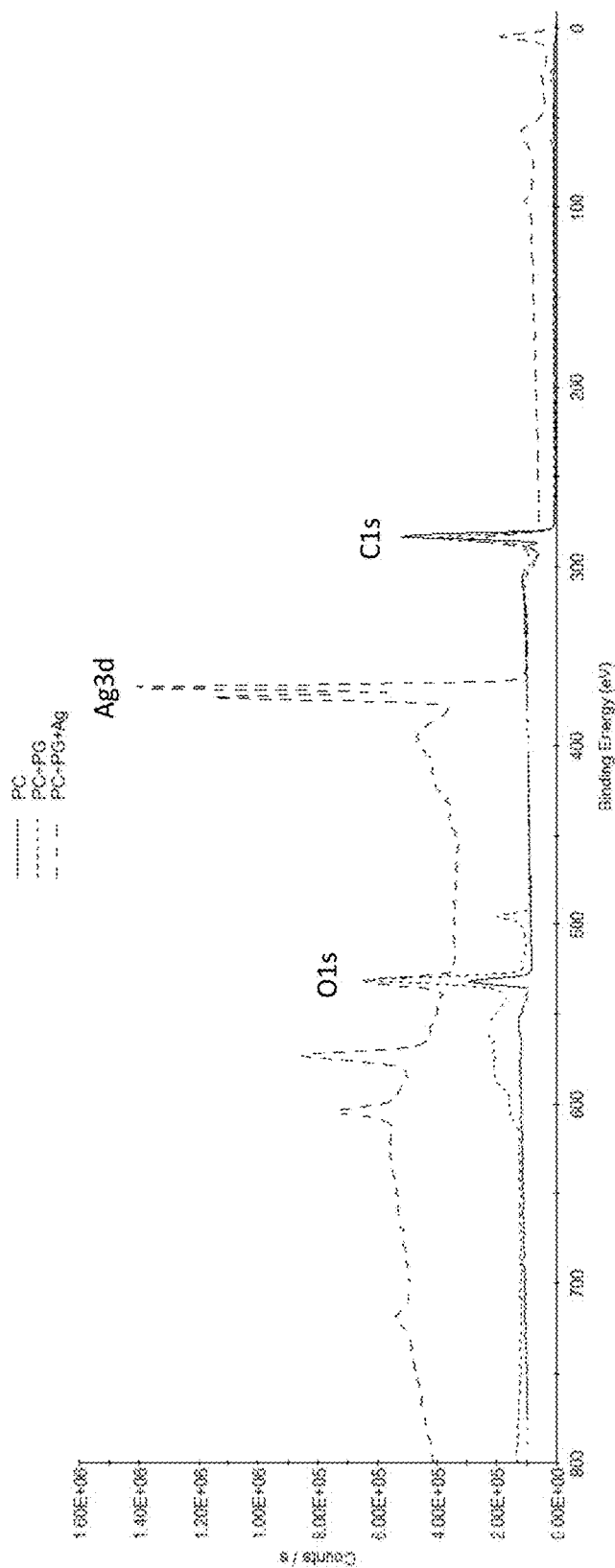
FIG. 10. XPS survey spectra of polycarbonate modified with pyrogallol and silver nitrate.

Surfaces modified with pyrogallol are capable of reducing ionic silver ($Ag^+$) from aqueous silver nitrate solutions. By "electroless", we mean an otherwise spontaneous process not requiring the use of an applied electric field to induce metallic coating formation. As-prepared substrates coated with pyrogallol are immersed in 100 mM $AgNO_3$ for 24 at room temperature with mild agitation. Upon visual inspection, polycarbonate substrates modified with pyrogallol and $AgNO_3$ appear dark amber in color (FIG. 8). Through scanning electron microscopy (SEM), metallic nanoparticle formation is observed on polytetrafluoroethylene substrates modified with pyrogallol and $AgNO_3$ (FIG. 9). Surface compositional analysis through XPS indicated incorporation of silver into the coating (FIG. 10 and Table 2), as seen by the emergence of Ag3d peaks.

TABLE 2

Elemental composition of polycarbonate (PC) modified with pyrogallol (PG) and silver nitrate (Ag), as determined by XPS.

| Surface | Elemental Composition | | | |
|---|---|---|---|---|
| | C1s | O1s | N1s | Ag3d |
| PC | 85.3% | 14.7% | 0.0% | 0.0% |
| PC + PG | 67.4% | 32.2% | 0.4% | 0.0% |
| PC + PG + Ag | 52.9% | 26.7% | 0.5% | 19.9% |

Figure 11:
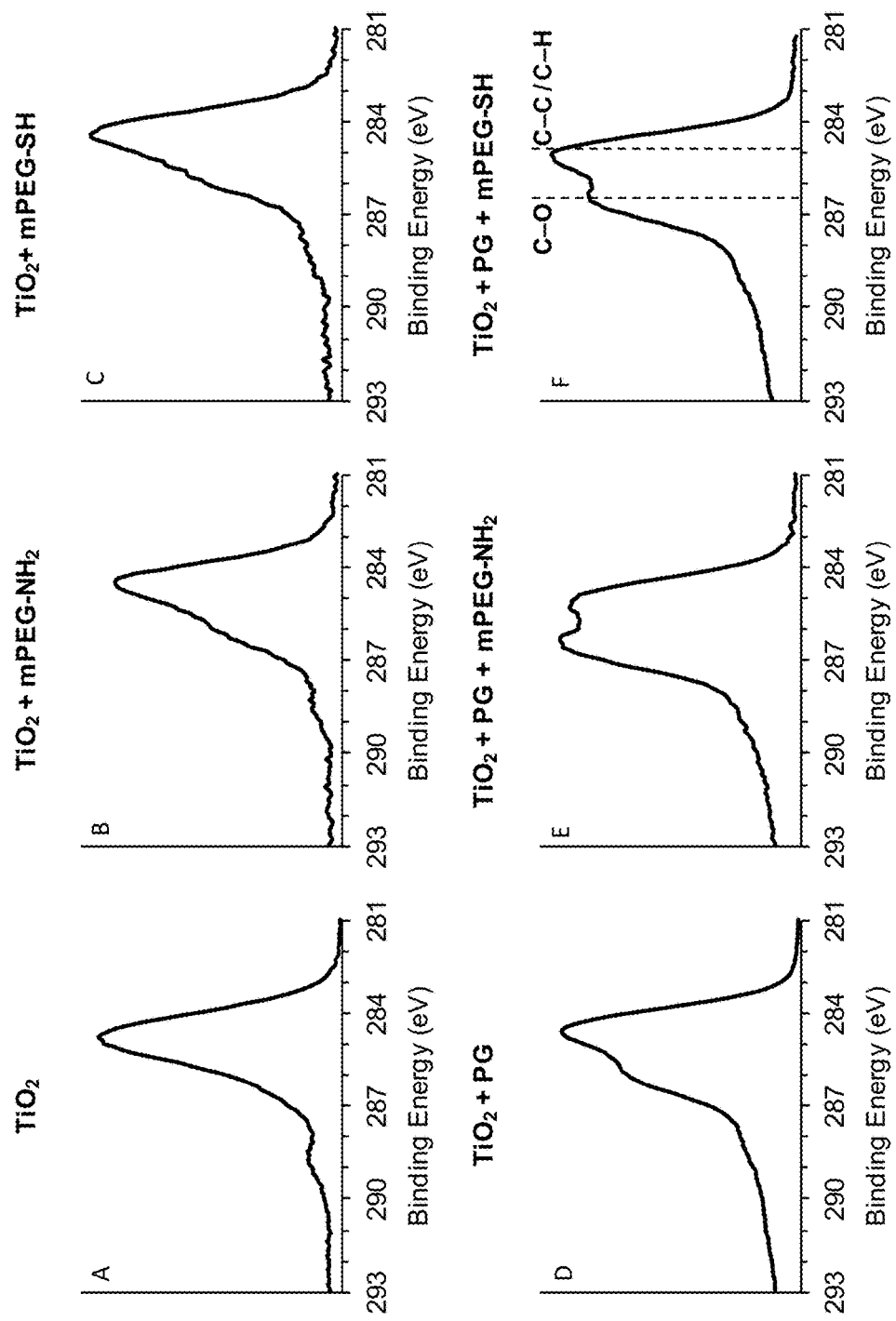
FIG. 11A. C1s detailed XPS spectra of a titanium dioxide ($TiO_2$) surface.
FIG. 11B. C1s detailed XPS spectra of a titanium dioxide ($TiO_2$) surface modified with mPEG-amine.
FIG. 11C. C1s detailed XPS spectra of a titanium dioxide ($TiO_2$) surface modified with mPEG-thiol.
FIG. 11D. C1s detailed XPS spectra of a titanium dioxide ($TiO_2$) surface modified with pyrogallol (PG).
FIG. 11E. C1s detailed XPS spectra of a titanium dioxide ($TiO_2$) surface modified with pyrogallol and mPEG-amine.
FIG. 11F. C1s detailed XPS spectra of a titanium dioxide ($TiO_2$) surface modified with pyrogallol and mPEG-thiol.

Substrates modified with pyrogallol were successfully functionalized with methoxy poly(ethylene glycol)-thiol (mPEG-SH) and methoxy poly(ethylene glycol)-amine (mPEG-$NH_2$). Following modification with pyrogallol, choice substrates were incubated in 1 mM mPEG-SH and mPEG-$NH_2$ solutions (5 k MW mPEG used), buffered at pH 8.5 with 10 mM bicine, for 10 minutes at room temperature with mild agitation. XPS analysis indicates that the emergence of C1s signal (286.7 eV) associated with C—O bonds occurs following incubation with mPEG in buffer (FIG. 11). Non-buffered solutions do not yield an appreciable change in the detailed C1s spectrum, relative to the unmodified polycarbonate control.

Additionally, we were able to perform co-incubations of pyrogallol with an 8-arm poly(ethylene glycol)-amine (8-arm PEG-amine), resulting in PEGylated coatings on polycarbonate. Pyrogallol and 8-arm PEG-amine (20 k MW) were combined in a 1:1 or 10:1 ratio of pyrogallol:amine group in an aqueous solution buffered at pH 7.8 with bicine, with or without 600 mM NaCl, for 18 h with shaking under room temperature. XPS analysis indicates a similar trend that has been seen when grafting mPEG-amine to a pyrogallol-modified substrate. 1:1 pyrogallol:amine with salt appears to result in the greatest PEG signature, as assessed by C1s signal, when compared to salt-free and 10:1 pyrogallol:amine conditions. Additionally, a nitrogen signal is detected for 1:1 pyrogallol:amine conditions using salt in the incubation solution (Table 3).

TABLE 3

Elemental composition of polycarbonate (PC) modified with pyrogallol (PG) and 8-arm PEG-amine, as determined by XPS.

| Surface | Elemental Composition | | |
|---|---|---|---|
| | C | O | N |
| PC | 85.3% | 14.7% | 0.0% |
| PC + 1:1 PG:amine − NaCl | 77.7% | 22.3% | 0.0% |
| PC + 1:1 PG:amine + NaCl | 73.1% | 25.4% | 1.3% |
| PC + 10:1 PG:amine − NaCl | 79.3% | 20.7% | 0.0% |
| PC + 10:1 PG:amine + NaCl | 76.5% | 23.3% | 0.2% |

The final concentrations were: 1:1 pyrogallol:amine—0.1 mg/mL pyrogallol and 2.0 mg/mL 8-arm PEG-amine and 10:1 pyrogallol:amine—1.0 mg/mL pyrogallol and 2.0 mg/mL 8-arm PEG-amine.

Subsequent exposure of mPEG-SH modified substrates to *Pseudomonas aeruginosa* (ATCC 7700) resulted in abrogated attachment of bacteria when compared to unmodified controls. The assay was performed by exposing the desired substrates to bacteria at $10^8$ CFU/mL in 0.85% NaCl solution for 24 h under static conditions. Following exposure, the resultant samples were rinsed, stained for bacteria, and the area coverage determined through fluorescence microscopy.

Example 4

Contact-mediated Antibacterial Properties of Pyrogallol-modified Surfaces

Figure 12:
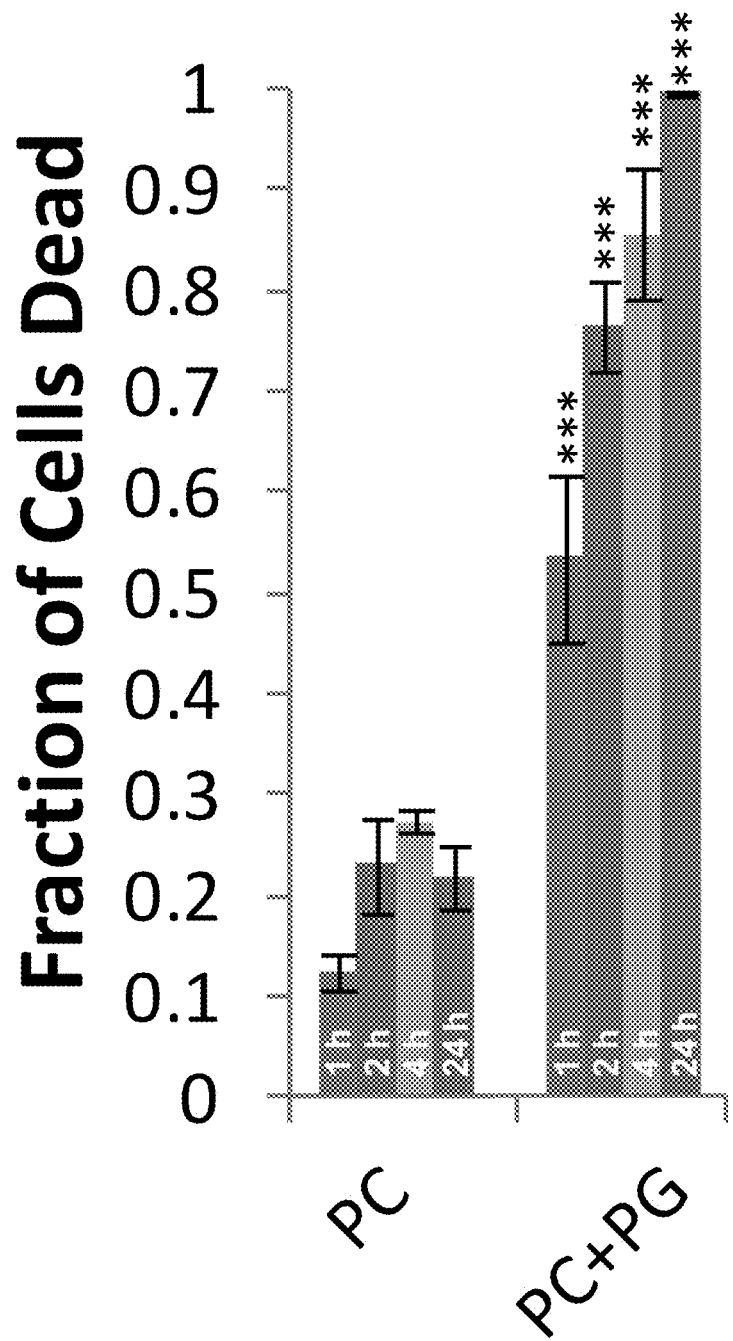
FIG. 12. Contact-mediated antibacterial behavior of pyrogallol-coated polycarbonate (PC) against *Pseudomonas aeruginosa*.

Polycarbonate substrates modified with 2 mg/mL pyrogallol for 8 h were exposed to *Pseudomonas aeruginosa* and *Staphylococcus aureus* for 24 h. Under the experimental conditions used, the *Pseudomonas aeruginosa* bacteria were in direct contact with the pyrogallol-modified surface (FIG. 12). Viability of the cells was assessed by using a live/dead stain (Invitrogen). A similar experiment was performed while maintaining cells away from the pyrogallol-modified surface, with no marked increase in antibacterial behavior observed relative to unmodified control surfaces. Based on the antibacterial data, it appears that the antibacterial properties of the pyrogallol-modified surfaces are contact-mediated.

Example 5

Superhydrophobic Surface Modifications Enabled Through Pyrogallol Coating

Superhydrophobic surfaces were generated as follows: Polystyrene beads (1 μm diameter) were deposited onto silicon wafer substrates with spin-coating. Pyrogallol was deposited onto the substrate surface as previously described. Silver nanoparticles were nucleated onto the entire pyrogallol-modified surface from aqueous silver nitrate solution. Alkanethiol solutions (5 mM octadecanethiol and 5 mM dodecanethiol in ethanol) were used to graft hydrophobic molecules to the resultant surfaces.

Figure 13:
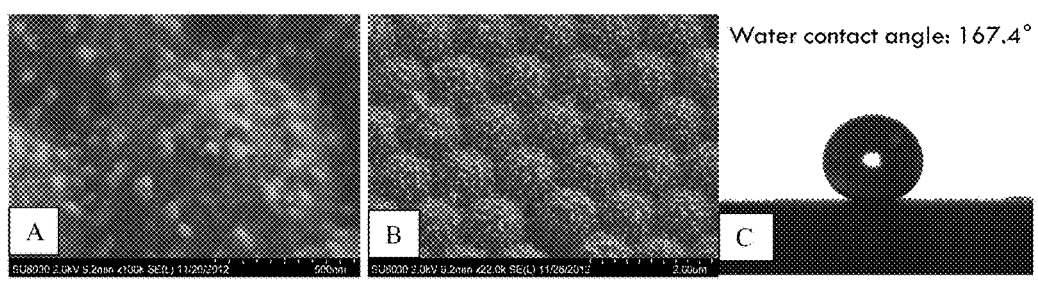
FIG. 13A. SEM micrograph of silicon surfaces modified with polystyrene beads, pyrogallol, silver, and octadecane thiol at high magnification.
FIG. 13B. SEM micrograph of silicon surfaces modified with polystyrene beads, pyrogallol, silver, and octadecanethiol at low magnification.
FIG. 13C. Image of the modified silicon surfaces with standing water droplet on the resultant superhydrophobic surface.

As assessed by scanning electron microscopy (SEM), the silicon surfaces modified with polystyrene beads, pyrogallol, silver nitrate, and alkanethiol indicate the presence of a hierarchical structure of micron- and nano-scale features, in an attempt to mimic the structure of the lotus leaf (FIG. 13). The measured contact angles exceed 150 degrees, classifying the resultant surface as superhydrophobic.

Example 6

Modification of Gold Nanorods with Pyrogallol and Subsequent Plasmon Tuning by Silver-shell Formation Gold nanorods, prepared by cetyltrimethylammonium bromide (CTAB)-templated synthesis, were modified with pyrogallol and subsequently metallized with a silver shell. The protocol for preparation of pyrogallol-coated gold nanorods, additionally modified with a silver shell, is as follows:

As-prepared CTAB-stabilized gold nanorods were centrifuged at 9,000 relative centrifugal force (rcf) for 10 minutes and the supernatant was discarded. The gold nanorod pellet was resuspended in 0.1 mg/mL pyrogallol buffered at pH 7.8 with 100 mM bicine without the addition of a metal salt, and sonicated for 20 minutes. For silver shell formation, 0-4,000 µM of AgNO$_3$ was added to the reaction mixture and the solution was sonicated for an additional 10 min.

Prior to centrifugation, the pyrogallol coating reaction is terminated by addition of concentrated acetic acid in a 1:1 molar ratio with bicine. Following centrifugation, the pyrogallol-coated gold nanorods are resuspended in water.

Figure 14:
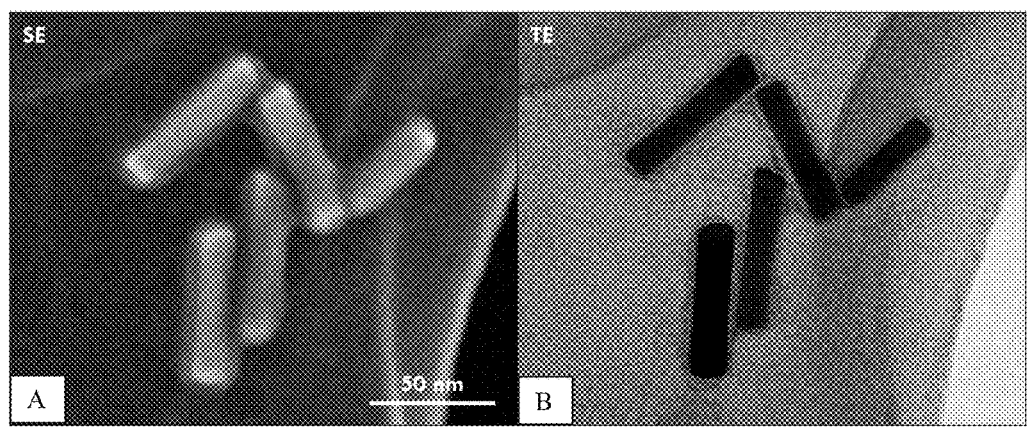
FIG. 14A. Secondary Electron (SE) mode illustrates the diffuse layer, likely attributable to bound pyrogallol, surrounding the gold nanorods core in STEM micrographs of gold nanorods modified with pyrogallol.
FIG. 14B. Transmission electron (TE) mode illustrates the diffuse layer, likely attributable to bound pyrogallol, surrounding the gold nanorods core in STEM micrographs of gold nanorods modified with pyrogallol.
Figure 15:
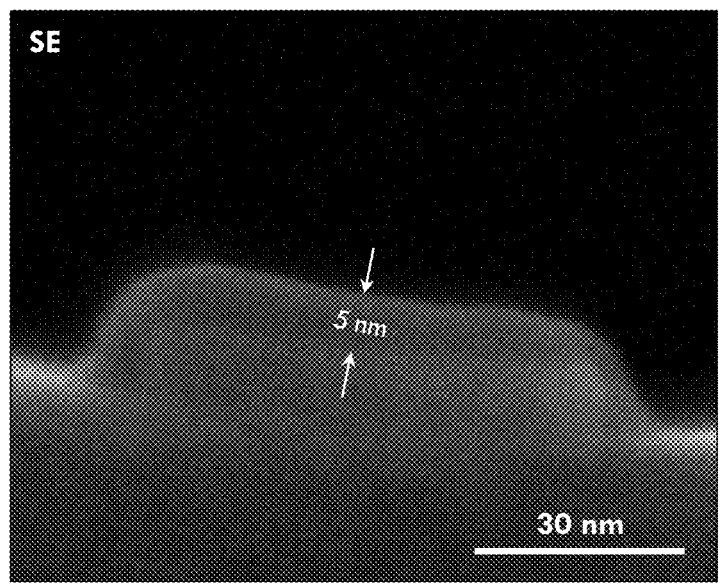
FIG. 15. STEM micrograph of a single gold nanorod modified with pyrogallol, obtained using secondary electron (SE) signal.
Figure 16:
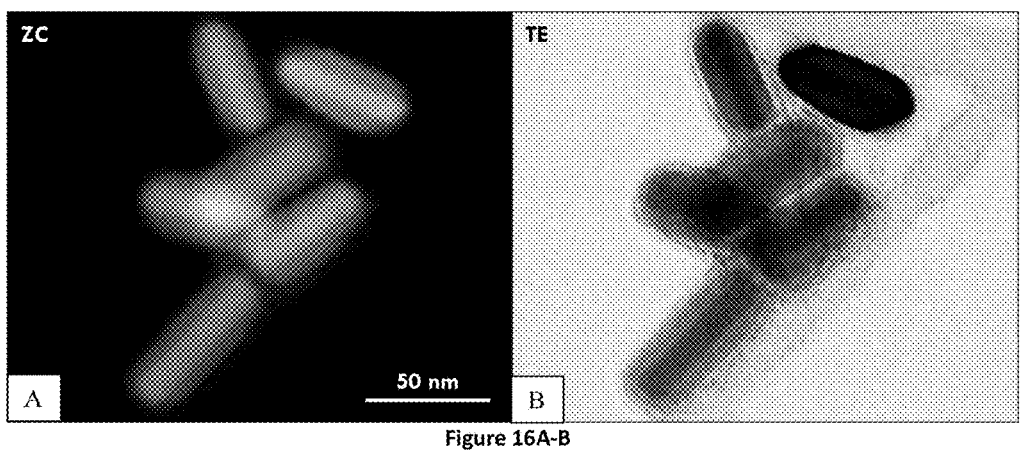
FIG. 16A. STEM micrographs of gold nanorods modified with pyrogallol.
FIG. 16B. STEM micrographs of gold nanorods modified with pyrogallol followed by incorporation of silver.
Figure 17:
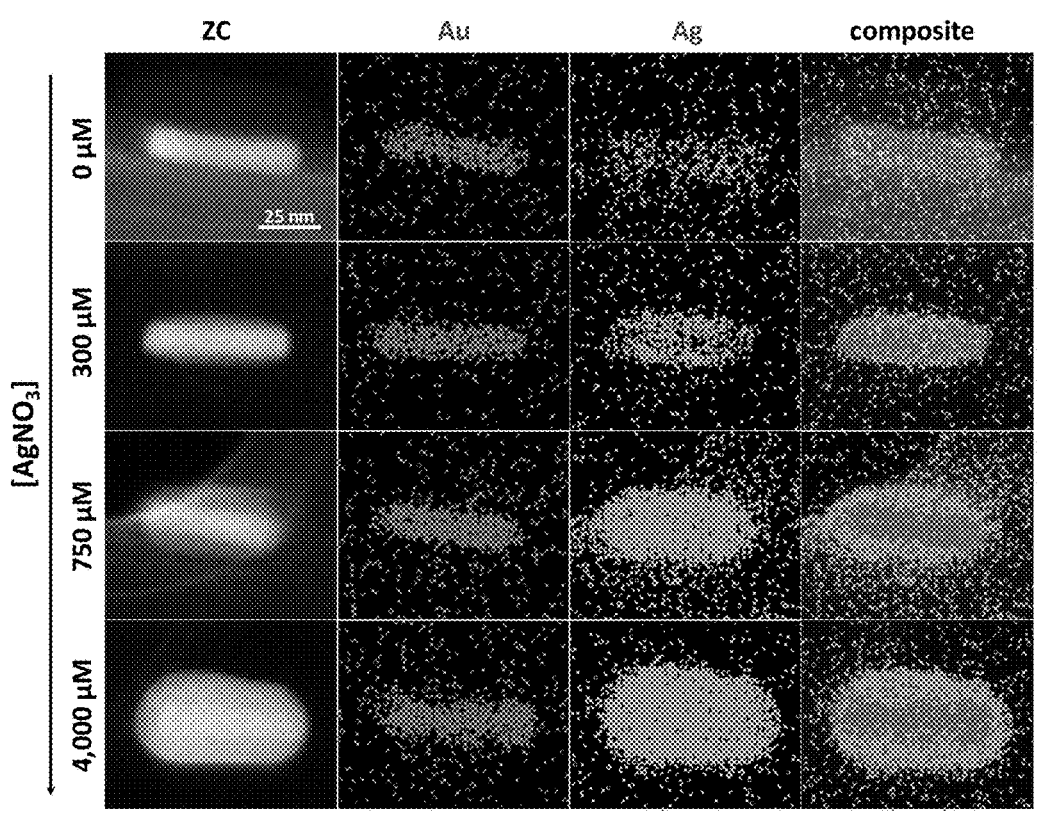
FIG. 17. EDS elemental composition maps of silver-shell gold-core nanorods formed via pyrogallol modification.

The pyrogallol-based layer was visible under secondary electron (SE) mode using scanning transmission electron microscopy (STEM) (FIG. 14), measuring approximately 5 nm in thickness (FIG. 15). The pyrogallol layer appears to stabilize the gold nanorods in solution without the need for an additional surfactant, like CTAB. The pyrogallol coating was utilized to deposit metallic silver on the gold nanorods surface. As seen by Z-contrast images through STEM, the less electron-dense silver metal surrounds the more electron-dense gold nanorods core (FIG. 16). Energy-dispersive electron spectroscopy (EDS) was utilized to confirm the silver-shell gold-core identity of the pyrogallol-modified gold nanorods constructs (FIG. 17).

Figure 18:
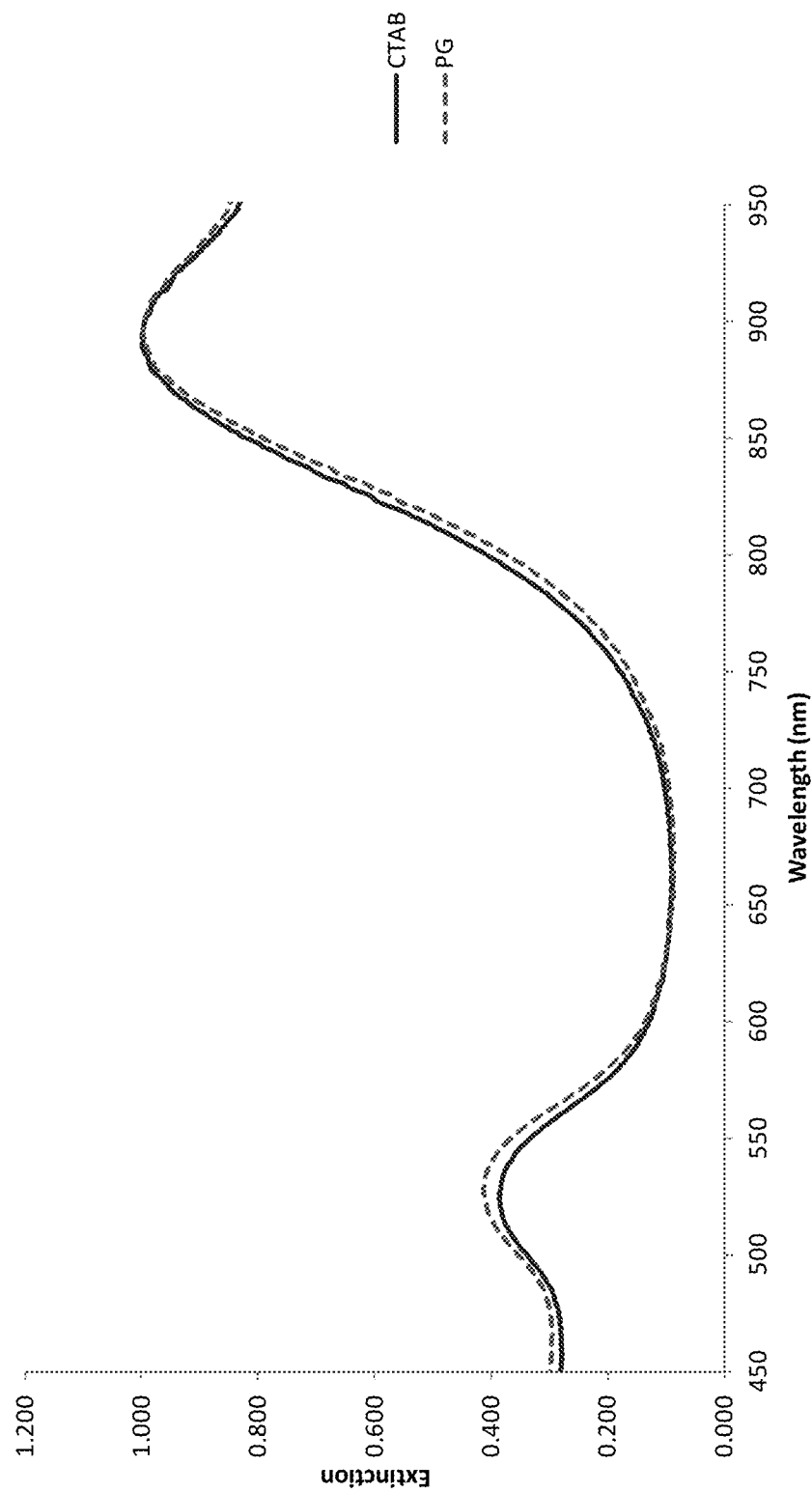
FIG. 18. UV-Vis spectrum sweeps for gold nanorods stabilized with cetyltrimethylammonium bromide (CTAB) and modified with pyrogallol.
Figure 19:
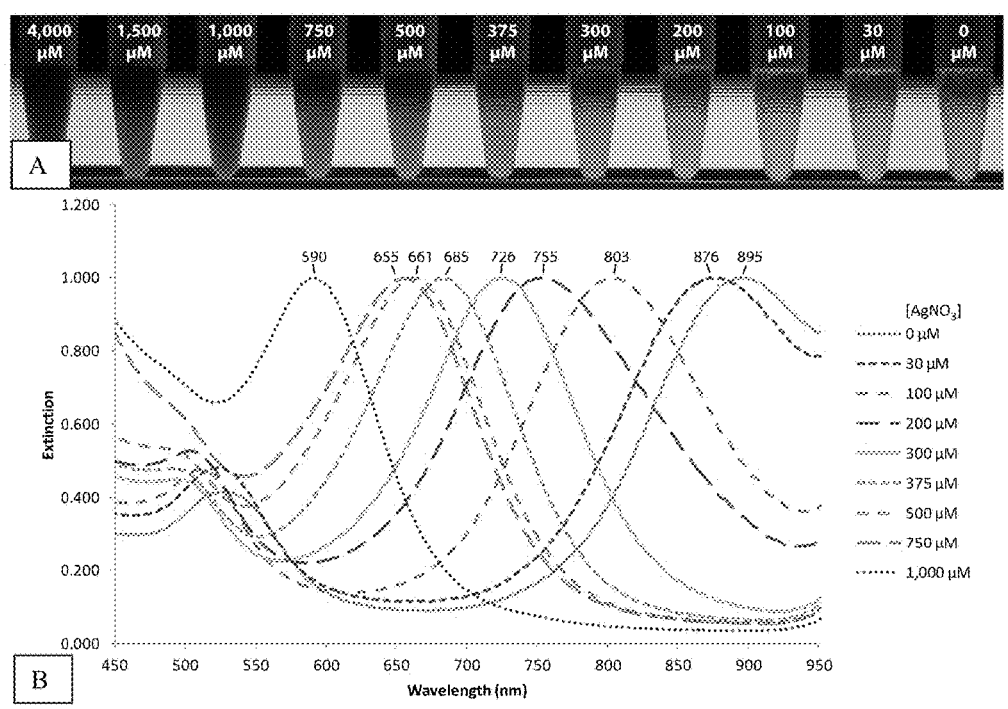
FIG. 19A. Gold nanorods plasmon tuning through silver-shell incorporation via pyrogallol. Solutions of gold nanorods modified with pyrogallol, followed by different concentrations of silver nitrate.
FIG. 19B. UV-Vis spectroscopy sweeps for silver-shell gold-core nanorods.

While the use of pyrogallol coatings alone does not dramatically alter the spectroscopic properties of gold nanorods (FIG. 18), the addition of a silver-shell can be used to tune the longitudinal plasmon wavelength for desired applications (FIG. 19). The thickness of the silver shell was influenced by the concentration of silver nitrate used during metallization (FIG. 17). Such plasmon wavelength tunability is attractive for designing metal nanorods excitable at specific wavelengths, for example, to match the emission properties of an available light source.

Example 7

Coating Ability at pH 3, 4, 5, 6, 7, 8, and 9

The ability to form coatings over a wide range of pH (3-9) values was confirmed. As an example, tannic acid was dissolved at a concentration of 1 mg/mL in solutions of 100 mM buffer and 600 mM NaCl at pH 7 (bis-Tris), 8 (bicine), and 9 (bicine). Pieces of titanium dioxide (TiO$_2$) were submerged in the tannic acid solutions, rocked for 24 h, rinsed thoroughly with water, and dried with N$_2$ gas. The coating ability was assessed via x-ray photoelectron spectroscopy (XPS) by monitoring the degree to which the Ti2p signal—corresponding to the underlying substrate (TiO$_2$)—was diminished (Table 4). If the best coating performance occurred at pH 7, a second round of coatings were conducted at pH 3 (formate), 4 (formate), 5 (acetate), and 6 (bis-Tris). The coating performance was assessed identically to what was described above.

The interpretation of the data is straightforward and based upon photoelectron escape from the sample. As a coating is deposited on top of the substrate, the photoelectrons representing the substrate are attenuated. Therefore the lower the substrate signal, the better the molecule was able to form a coating. Coatings greater than approximately 10 nm in thickness entirely eliminate the signal from the substrate because the photoelectrons cannot escape and be detected. In Table 4, a value of 100% indicates no coating formation, and a value of 0% indicates at least 10 nm of coating.

Using this strategy, tannic acid, epigallocatechin gallate (EGCG), pyrogallol (PG), hydroxyhydroquinone (HHQ), gallic acid, ellagic acid, catechin, epigallocatechin (EGC), morin, quercetin, naringenin, naringin, rutin, phloroglucinol, catechol, resorcinol, hydroquinone, phenol, and resveratrol were investigated. Tannic acid, EGCG, PG, HHQ, catechin, EGC, morin, quercetin, naringenin, naringin, rutin, phloroglucinol, catechol, resorcinol, hydroquinone, and phenol (all molecules other than gallic acid, ellagic acid, resorcinol, and resveratrol) were found to be capable of forming coatings between pH 3 and 9.

TABLE 4

Ti2p signal strength after coating TiO$_2$ sample with candidate molecules.

| Molecule | Ti2p Signal Strength (%) | | | | | | |
|---|---|---|---|---|---|---|---|
| | pH 3 | pH 4 | pH 5 | pH 6 | pH 7 | pH 8 | pH 9 |
| Gallic acid | d | d | d | d | 94.0 | 95.0 | 88.3 |
| Tannic acid | 65.2 | 56.8 | 62.9 | 0.0 | 0.0 | 62.9 | 72.7 |
| Ellagic acid | d | d | d | d | c | c | c |
| Catechin | d | d | d | d | 44.9 | 49.0 | 0.0 |
| EGC (0.1 mg/mL) | d | d | d | d | 90.2 | 84.1 | 41.2 |
| EGCG (0.1 mg/mL) | 81.5 | 87.4 | 82.5 | 52.4 | 8.7 | 43.8 | 91.8 |
| EGCG | 70.1 | 71.5 | 71.8 | 67.7 | 0.3 | 45.5 | 83.8 |
| Morin | d | d | d | d | c | 45.9 | 54.7 |
| Quercetin | d | d | d | d | c | c | 73.3 |
| Naringenin | d | d | d | d | c | 80.2 | 90.1 |
| Naringin | d | d | d | d | 90.9 | 79.0 | 80.0 |
| Rutin | d | d | d | d | c | 65.1 | 88.0 |
| Phloroglucinol | d | d | d | d | 98.0 | 82.8 | 77.4 |
| PG | 100.9 | 96.6 | 87.6 | 35.3 | 11.0 | 58.0 | 86.9 |
| Catechol | d | d | d | d | 51.7 | 8.5 | 81.1 |
| Resorcinol | d | d | d | d | 94.7 | 85.0 | 90.9 |
| Hydroquinone | d | d | d | d | 89.3 | 89.6 | 70.6 |
| HHQ | 18.6 | 32.9 | 22.0 | 1.1 | 51.6 | 88.2 | 76.8 |
| Phenol | d | d | d | d | 102.2 | 68.5 | 79.0 |
| Resveratrol (0.5 mg/mL) | d | d | d | d | c | 97.7 | 95.3 |
| Buffer Controls | 86.5 | 85.3 | 91.7 | 90.7 | 100 | 97.3 | 92.8 |

[a] All coating precursors were dissolved at 1 mg/mL unless otherwise indicated.
[b] Values associated with successful coatings (at least 20% signal reduction) are in bold.
[c] Represents insolubility of the precursor.
[d] Represents conditions that were not investigated (explained in Example 7).

In order to further corroborate XPS results, select molecules were further studied via ellipsometry for their ability to form coatings. Compounds were tested at their optimal pH conditions, which were defined as the pH that caused the greatest signal attenuation in the XPS trials (represented in Table 1). As an example, tannic acid was dissolved at a concentration of 1 mg/mL in solutions of 100 mM bis-Tris and 600 mM NaCl at pH 7. Three TiO$_2$ samples were submerged in the tannic acid solutions, rocked for 24 h, rinsed thoroughly with water, and dried with N$_2$ gas. Coating thickness was then measured by ellipsometry (Table 5).

Following a similar procedure, tannic acid, pyrogallol, catechol, catechin, HHQ, EGCG, and morin were coated at pH 6, 7, 8, 9, 6, 7, and 8, respectively. Tannic acid was tested at pH 6 and 7 because both led to 100% Ti2p signal reduction in Example 7. Coating thicknesses were determined via ellipsometry, as explained above.

When phenolic compounds were omitted (buffer controls), no coating was observed at any pH.

TABLE 5

Coating thickness (nm) on $TiO_2$ and polycarbonate as determined by ellipsometry.

| Substrate | Coating Precursor | Conditions | Coating Thickness (nm) |
|---|---|---|---|
| $TiO_2$ | Tannic acid | 24 h, pH 6 | 5.8 ± 0.9 |
| | Tannic acid | 24 h, pH 7 | 109.3 ± 7.1 |
| | Pyrogallol | 24 h, pH 7 | 19.0 ± 1.9 |
| | Catechol | 48 h, pH 8 | 5.0 ± 0.1 |
| | Catechin | 48 h, pH 9 | 250.3 ± 51.8 |
| | Hydroxyhydroquinone | 48 h, pH 6 | 48.8 ± 10.5 |
| | Epigallocatechin gallate | 48 h, pH 7 | 34.3 ± 7.2 |
| | Morin | 48 h, pH 8 | 1.9 ± 0.2 |

Example 8

Determination of Coloration Caused by Coating

Figure 20:
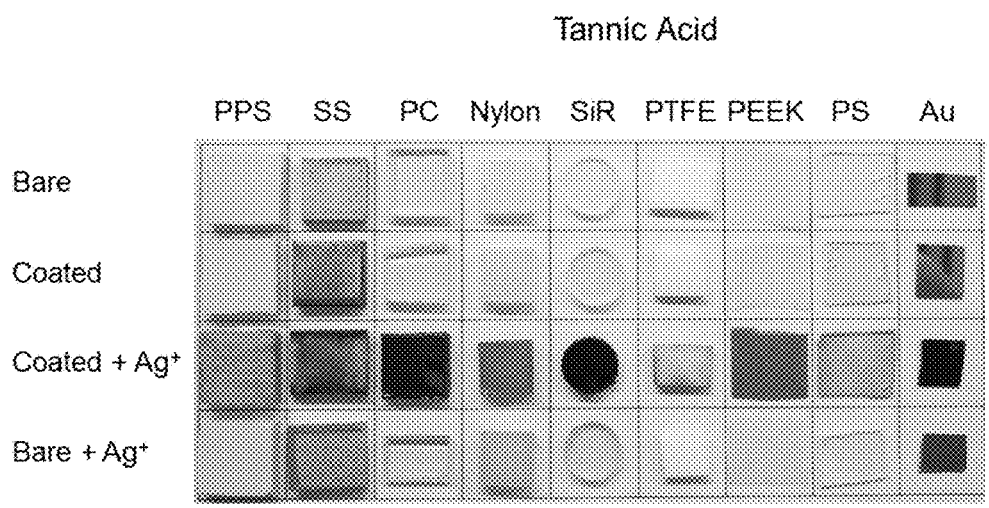
FIG. 20. TA coatings (with and without silver) on various materials.

In order to determine the discoloration caused by phenolic coatings, several materials were modified with phenolic films. Representative examples were chosen from metals, metal oxides, organic polymers, inorganic polymers, and bulk materials. Substrates include $TiO_2$, silica wafer with a thermal oxide layer ($SiO_2$), gold (Au), polycarbonate (PC), polytetrafluoroethylene (PTFE), polystyrene (PS), nylon 6-12, poly(ether ether ketone) (PEEK), poly(p-phenylene sulfide) (PPS), and stainless steel (SS). As an example, tannic acid was dissolved at a concentration of 1 mg/mL in solutions of 100 mM bis-Tris and 600 mM NaCl at pH 7. Samples were submerged in the tannic acid solutions, rocked for 24 h, rinsed thoroughly with water, and dried with $N_2$ gas. Coatings were revealed by reacting with silver nitrate ($Ag^+$) and recorded visually through digital photography (FIG. 20).

Figure 21:
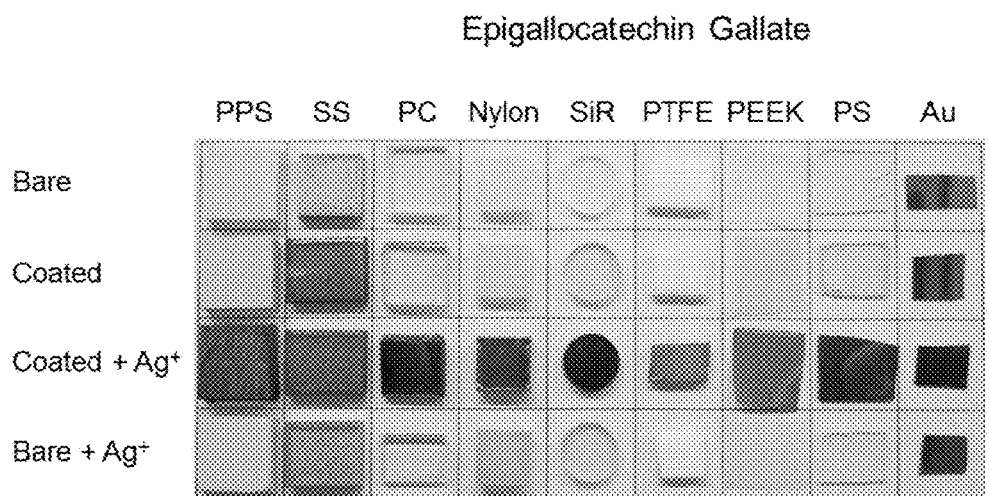
FIG. 21. EGCG coatings (with and without silver) on various materials.

Following a similar procedure, various materials were coated with PG at pH 7, catechol at pH 8, catechin at pH 9, HHQ at pH 6, and EGCG at pH 7. Representative results are shown in FIG. 21 for coatings derived from EGCG.

Example 9

Substrate-independent Coatings

In order to determine the ability of coatings to form, independent of the substrate composition, several materials were investigated. Representative examples were chosen from metals, metal oxides, organic polymers, inorganic polymers, and bulk materials. Substrates include $TiO_2$, silica wafer with a thermal oxide layer ($SiO_2$), gold (Au), polycarbonate (PC), polytetrafluoroethylene (PTFE), polystyrene (PS), nylon 6-12, poly(ether ether ketone) (PEEK), poly(p-phenylene sulfide) (PPS), and stainless steel (SS). Tannic acid was dissolved at a concentration of 1 mg/mL in solutions of 100 mM bis-Tris and 600 mM NaCl at pH 7. Samples were submerged in the tannic acid solutions, rocked for 24 h, rinsed thoroughly with water, and dried with $N_2$ gas. The presence of a coating was determined by XPS and by silver deposition (Table 6).

Following a similar procedure, various materials were coated with PG, catechol, catechin, HHQ, and EGCG at pH 7, 8, 9, 6, and 7, respectively. Coating ability was determined by XPS, ellipsometry, and silver deposition. Notably, although the tested compounds coated a wide variety of materials, none of the compounds tested were capable of coating a silica wafer (or glass).

TABLE 6

Coating ability on a wide range of substrate materials.

| Coating Precursor | Coating Formed? | | | | | | | | | |
|---|---|---|---|---|---|---|---|---|---|---|
| | $TiO_2$ | $SiO_2$ | Au | PC | PTFE | PS | Nylon | PEEK | PPS | SS |
| TA | Yes | No | Yes | Yes | Yes | Yes | Yes | Yes | Yes | Yes |
| PG | Yes | No | Yes | Yes | Yes | Yes | Yes | Yes | Yes | Yes |
| Catechol | Yes | No | Yes | Yes | Yes | Yes | Yes | Yes | Yes | Yes |
| Catechin | Yes | No | Yes | Yes | Yes | Yes | Yes | Yes | Yes | Yes |
| HHQ | Yes | No | Yes | Yes | Yes | Yes | Yes | Yes | Yes | Yes |
| EGCG | Yes | No | Yes | Yes | Yes | Yes | Yes | Yes | Yes | Yes |

[a] The presence of a coating was confirmed by XPS, ellipsometry, and silver deposition, as described in Example 7.
[b] $TiO_2$—titanium dioxide; $SiO_2$—silica; Au—gold; PC—polycarbonate; PTFE—polytetrafluoroethylene; PS—polystyrene; Nylon—nylon 6-12; PEEK—poly(ether ether ketone); PPS—poly(p-phenylene sulfide); SS—stainless steel.

Example 10

Relating $pK_a$ to Coating pH

In order to investigate the relationship between coating pH and deprotonation, coating precursor molecules were studied via potentiometric titrations. A solution of tannic acid was made by dissolving ~1 mg in 2 mL of 100 mM KCl in a glass test tube to perform the titration. The TA and KOH solutions were degassed by aggressively sparging argon for no less than 30 min. Base was titrated in 1.0 µL increments, and the total amount added was 250 µL. If oxygen is purged correctly, the phenolic solution should display little or no change in color throughout the titration. The first $pK_a$ was calculated by initially plotting the volume of base added versus pH. The first derivative of this curve was then plotted as a function of pH, and the $pK_a$ was calculated by determining the pH associated with any local maxima.

Following a similar procedure, the first $pK_a$ values for PG, catechol, catechin, HHQ, and EGCG were determined via potentiometric titration (Table 7).

TABLE 7

$pK_a$ and optimal coating pH values associated with coating precursors.

| Molecule | First $pK_a$ | Optimal Coating pH | $pK_a$ – pH |
|---|---|---|---|
| Catechin | 9.2 | 9.0 | 0.2 |
| TA | 7.7 | 7.0 | 0.7 |
| EGCG | 8.1 | 7.0 | 1.1 |
| Catechol | 9.5 | 8.0 | 1.5 |
| PG | 9.3 | 7.0 | 2.3 |
| HHQ | 9.1 | 6.0 | 3.1 |

Based on the data from Examples 7-10, no one pH exists as an optimal condition for forming polyphenol-based coatings. Additionally, based on the data from Table 7, the optimal pH cannot be determined by relating coating pH to the $pK_a$ of the precursor molecule. Taking these two observations into account, the overall theme is that each molecule must be optimized independently.

Example 11

Stability of Phenolic Coatings

Figure 22:
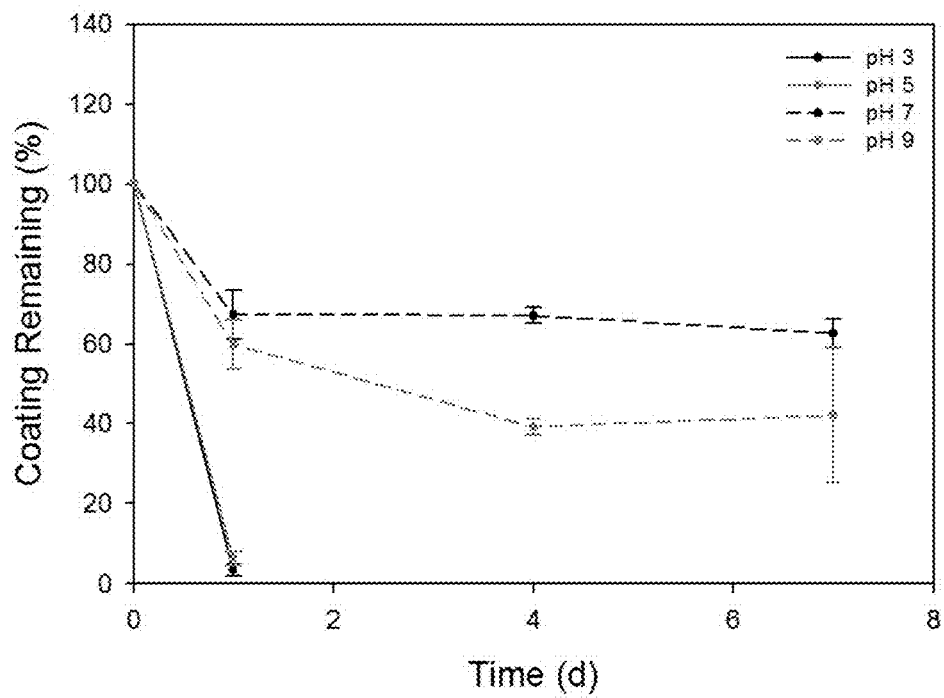
FIG. 22. Graph showing stability of TA-based coatings.

In order to determine the stability of phenolic coatings in aqueous conditions, coated samples were incubated in buffers for several days. Tannic acid was dissolved at a concentration of 1 mg/mL in solutions of 100 mM bis-Tris and 600 mM NaCl at pH 7. Three polycarbonate samples were submerged in the tannic acid solutions, rocked for 24 h, rinsed thoroughly with water, and dried with $N_2$ gas. The coating thickness was determined via ellipsometry. Coated samples were then submerged in 50 mM buffer solutions at pH 3 (formate), 5 (acetate), 7 (PBS), or 9 (bicine). At day 1, 4, and 7, samples were removed from buffers, rinsed thoroughly with water, and dried with $N_2$ gas. The coating thickness that remained was calculated via ellipsometry, and stability was based on the percentage of the initial coating thickness that was present at day 1, 4, and 7 (FIG. 22).

Figure 23:
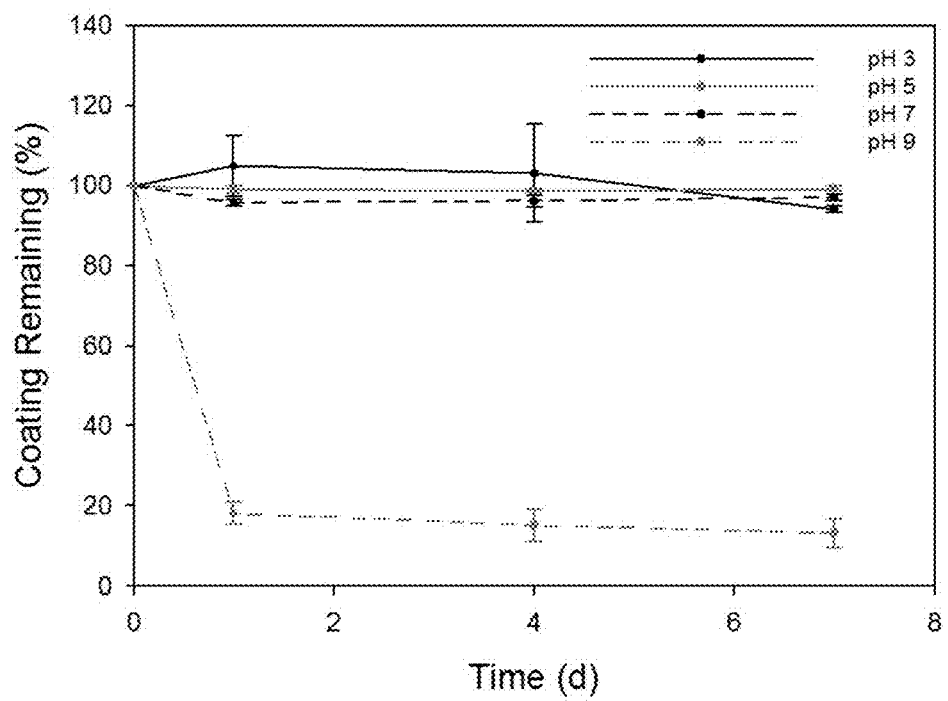
FIG. 23. Graph showing stability of catechin-based coatings.

Following a similar procedure, the stabilities of coatings based on pyrogallol, catechol, catechin (FIG. 23), HHQ, and EGCG were investigated.

Example 12

Effect of Salt on Coating Formation

The effect of salt composition on coating formation was investigated at optimal pH conditions identified previously for each molecule. As an example, gallic acid was dissolved at a concentration of 1 mg/mL in solutions of 100 mM bis-Tris at pH 7 containing 600 mM NaCl, 600 mM $MgCl_2$, 600 mM $CaCl_2$, 100 µM $CuCl_2$ with 600 mM NaCl, or 100 µM $ZnCl_2$ with 600 mM NaCl. Pieces of titanium dioxide ($TiO_2$) or silicon dioxide ($SiO_2$) were submerged in the gallic acid solutions, rocked for 48 h, rinsed thoroughly with water, and dried with $N_2$ gas. The coating ability was assessed via x-ray photoelectron spectroscopy (XPS) by monitoring the degree to which the substrate signal—Ti2p for $TiO_2$ and Si2p for $SiO_2$—was diminished (Tables 8-9). The results indicate that gallic acid solutions produced coatings on $SiO_2$ and $TiO_2$ in buffers containing $MgCl_2$ or $CaCl_2$, but not in NaCl-based buffers. None of coating precursor molecules were able to coat $SiO_2$ when dissolved in NaCl-based buffers.

As before, the interpretation of the data is straightforward and based upon photoelectron escape from the sample. As a coating is deposited on top of the substrate, the photoelectrons representing the substrate are attenuated. Therefore the lower the substrate signal, the better the molecule was able to form a coating. Coatings greater than approximately 10 nm in thickness entirely eliminate the signal from the substrate because the photoelectrons cannot escape and be detected. Using this strategy, gallic acid, tannic acid, catechin, epigallocatechin gallate (EGCG), quercetin, phloroglucinol, pyrogallol (PG), catechol, resorcinol, hydroquinone, hydroxyhydroquinone (HHQ), and phenol—all molecules tested—were able to coat both $TiO_2$ and $SiO_2$ with at least one of the experimental conditions described here.

TABLE 8

Ti2p signal strength after immersing $TiO_2$ in buffered solution containing precursor molecules.

| | Ti2p Signal Strength (%) | | | | |
|---|---|---|---|---|---|
| Molecule | $Na^+$ | $Mg^{2+}$ | $Ca^{2+}$ | $Cu^{2+}$ | $Zn^{2+}$ |
| Gallic acid, pH 7 | 107.6 | 0.0 | 0.0 | 106.3 | 80.7 |
| Tannic acid, pH 6 | e | 0.0 | 0.0 | e | e |
| Tannic acid, pH 7 | 0.0 | 88.9 | 11.4 | 0.0 | 0.0 |
| Catechin, pH 9 | 0.0 | 0.0 | 0.0 | 0.0 | 0.0 |
| EGCG, pH 7 | 0.0 | 0.0 | 0.0 | 0.0 | 13.0 |
| Quercetin, pH 9 | 83.9 | 54.6 | 0.0 | 94.4 | 77.6 |
| Phloroglucinol, pH 8 | 94.8 | 84.7 | 106.8 | 94.7 | 91.9 |
| Phloroglucinol, pH 9 | 88.6 | 51.6 | 81.7 | 94.4 | 111.9 |
| PG, pH 7 | 12.6 | 0.0 | 0.0 | 0.0 | 3.9 |
| Catechol, pH 8 | 9.7 | 0.0 | 0.0 | 89.8 | 93.5 |
| Resorcinol, pH 8 | 97.3 | 0.0 | 111.6 | 84.1 | 104.7 |
| Hydroquinone, pH 9 | 80.8 | 62.5 | 0.0 | 93.5 | 108.7 |
| HHQ, pH 6 | 0.0 | 0.0 | 0.0 | 14.1 | 5.0 |
| Phenol, pH 8 | 78.5 | 0.0 | 106.8 | 78.7 | 86.4 |

$^a$ $Na^+$ = 600 mM NaCl; $Mg^{2+}$ = 600 mM $MgCl_2$; $Ca^{2+}$ = 600 mM $CaCl_2$; $Cu^{2+}$ = 100 µM $CuCl_2$ + 600 mM NaCl; $Zn^{2+}$ = 100 µM $ZnCl_2$ + 600 mM NaCl.
$^b$ pH 6 & 7 = 100 mM bis-Tris; pH 8 & 9 = 100 mM bicine.
$^c$ All coating precursors were dissolved at 1 mg/mL
$^d$ Values associated with successful coatings (at least 20% signal reduction) are in bold.
e Represents conditions that were not investigated.

TABLE 9

Si2p signal strength after immersing $SiO_2$ in buffered solution containing precursor molecules.

| | Si2p Signal Strength (%) | | | | |
|---|---|---|---|---|---|
| Molecule | $Na^+$ | $Mg^{2+}$ | $Ca^{2+}$ | $Cu^{2+}$ | $Zn^{2+}$ |
| Gallic acid, pH 7 | 95.3 | 0.0 | 7.7 | 91.0 | 107.5 |
| Tannic acid, pH 6 | e | 83.8 | 102.7 | e | e |
| Tannic acid, pH 7 | 111.9 | 50.3 | 105.4 | 103.0 | 90.6 |
| Catechin, pH 9 | 107.1 | 0.0 | 99.2 | 105.7 | 81.7 |
| EGCG, pH 7 | 108.5 | 20.6 | 99.8 | 107.1 | 104.1 |
| Quercetin, pH 9 | 90.2 | 7.8 | 0.0 | 88.5 | 95.1 |
| Phloroglucinol, pH 8 | 85.3 | 69.4 | 91.7 | 83.9 | 88.7 |
| Phloroglucinol, pH 9 | 30.5 | 76.5 | 84.6 | 78.9 | 90.4 |
| PG, pH 7 | 100.1 | 0.0 | 2.2 | 106.5 | 108.7 |
| Catechol, pH 8 | 108.7 | 0.0 | 0.0 | 72.4 | 76.9 |
| Resorcinol, pH 8 | 89.9 | 71.6 | 88.7 | 76.9 | 90.6 |
| Hydroquinone, pH 9 | 85.9 | 77.1 | 86.5 | 68.2 | 89.0 |

TABLE 9-continued

Si2p signal strength after immersing SiO$_2$ in buffered solution containing precursor molecules.

| Molecule | Si2p Signal Strength (%) | | | | |
|---|---|---|---|---|---|
| | Na$^+$ | Mg$^{2+}$ | Ca$^{2+}$ | Cu$^{2+}$ | Zn$^{2+}$ |
| HHQ, pH 6 | 94.9 | 80.5 | 1.5 | 93.5 | 104.8 |
| Phenol, pH 8 | 93.0 | 0.0 | 70.8 | 71.9 | 85.6 |

$^a$ Na$^+$ = 600 mM NaCl; Mg$^{2+}$ = 600 mM MgCl$_2$; Ca$^{2+}$ = 600 mM CaCl$_2$; Cu$^{2+}$ = 100 μM CuCl$_2$ + 600 mM NaCl; Zn$^{2+}$ = 100 μM ZnCl$_2$ + 600 mM NaCl.
$^b$ pH 6 & 7 = 100 mM bis-Tris; pH 8 & 9 = 100 mM bicine.
$^c$ All coating precursors were dissolved at 1 mg/mL.
$^d$ Values associated with successful coatings (at least 20% signal reduction) are in bold.
e Represents conditions that were not investigated.

Figure 24:
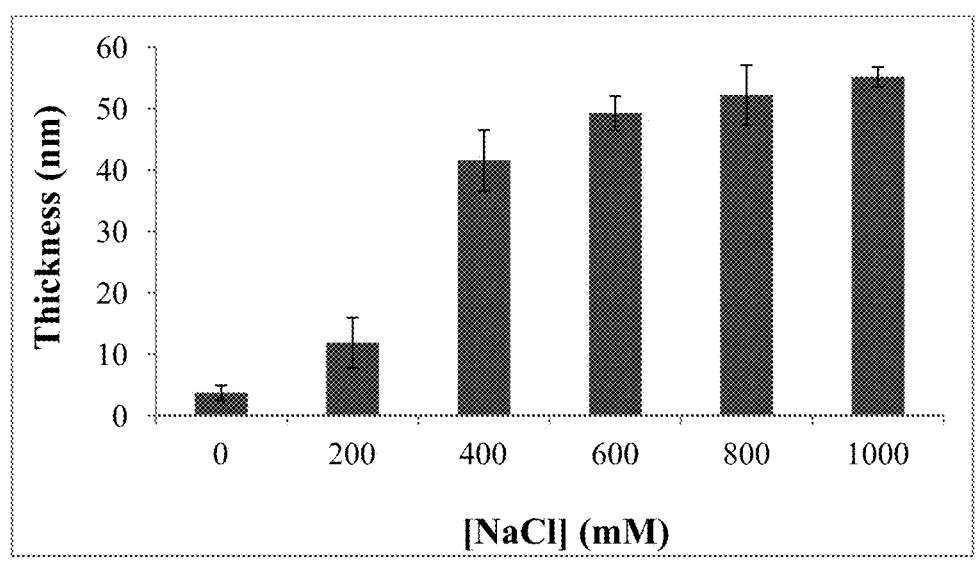
FIG. 24. Bar graph showing effect of sodium chloride (NaCl) concentration on PG-based coating thickness. Conditions: 2 mg/mL PG in 100 mM bis-Tris at pH 7 with varying amounts of NaCl.

In this Example, we included other salts, salt concentrations and pH ranges employed during coating solution. FIG. 24 shows the effect of sodium chloride (NaCl) concentration on PG-based coating thickness. Conditions: 2 mg/mL PG in 100 mM bis-Tris at pH 7 with varying amounts of NaCl.

Figure 25:
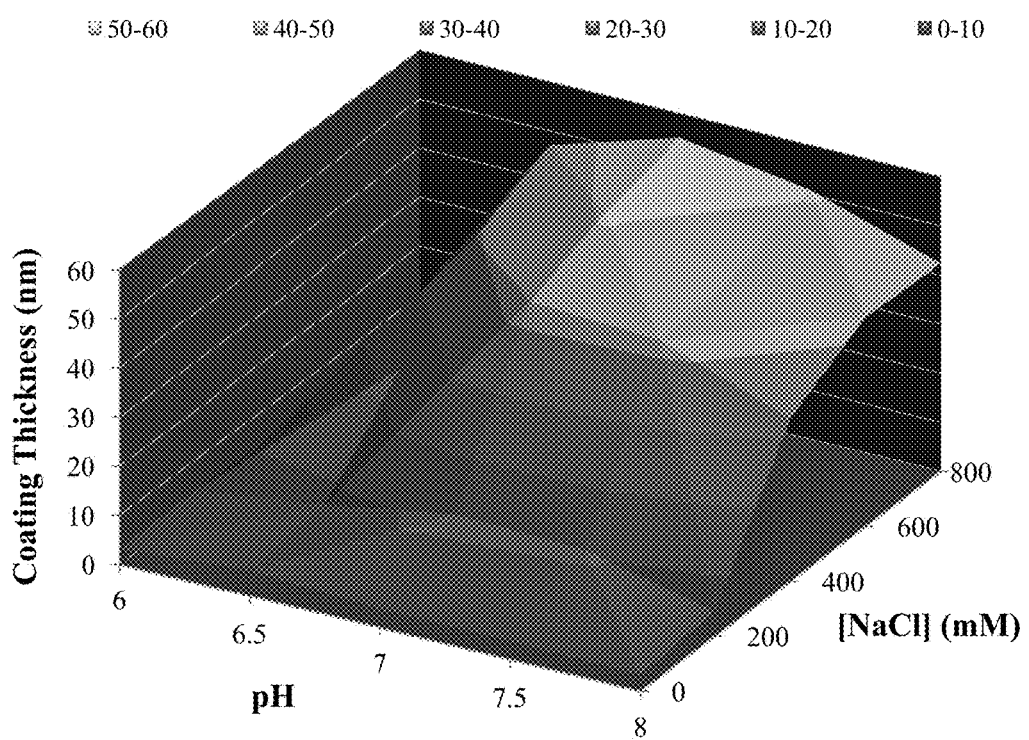
FIG. 25. Graph showing effect of sodium chloride (NaCl) concentration and pH on PG-based coating thickness. Conditions: 2 mg/mL PG in 100 mM buffer (bis-Tris or bicine, depending on pH) with varying pH and varying amounts of NaCl. The numbers at the top of the figure correlate coating thickness to color.

FIG. 25 shows the effect of sodium chloride (NaCl) concentration and pH on PG-based coating thickness. Conditions: 2 mg/mL PG in 100 mM buffer (bis-Tris or bicine, depending on pH) with varying pH and varying amounts of NaCl. The numbers at the top of the figure correlate coating thickness to color.

Figure 26:
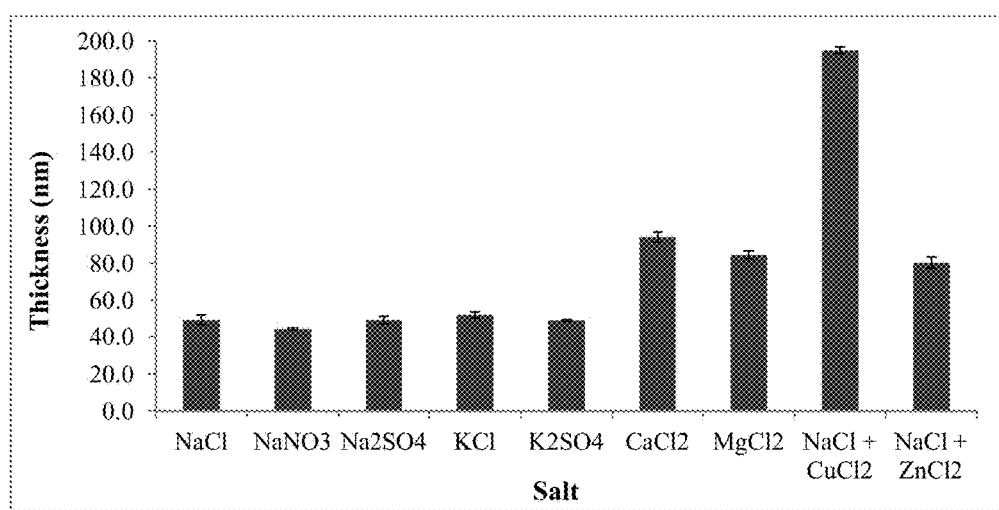
FIG. 26. Graph showing effect of salt choice on PG-based coating thickness. Conditions: 2 mg/mL PG in 100 mM bis-Tris at pH 7 with 600 mM salt. Coating conditions: 2 mg/mL PG in 100 mM bis-Tris with salt at pH 7, 8 h. All salts were at a concentration of 600 mM, except $CuCl_2$ and $ZnCl_2$. These two salts were added at a concentration of 100 μM to 600 mM NaCl.

FIG. 26 shows the effect of salt choice on PG-based coating thickness. Conditions: 2 mg/mL PG in 100 mM bis-Tris at pH 7 with 600 mM salt. Coating conditions: 2 mg/mL PG in 100 mM bis-Tris with salt at pH 7, 8 h. All salts were at a concentration of 600 mM, except CuCl$_2$ and ZnCl$_2$. These two salts were added at a concentration of 100 μM to 600 mM NaCl.

Figure 27:
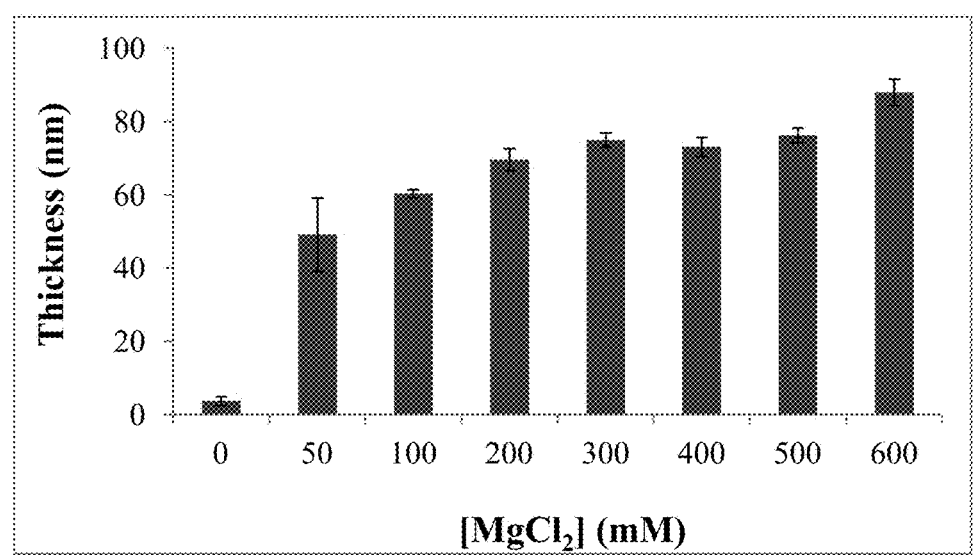
FIG. 27. Bar graph showing effect of magnesium chloride ($MgCl_2$) concentration on PG-based coating thickness. Conditions: 2 mg/mL PG in 100 mM bis-Tris at pH 7 with varying amounts of $MgCl_2$.

FIG. 27 shows the effect of magnesium chloride (MgCl$_2$) concentration on PG-based coating thickness. Conditions: 2 mg/mL PG in 100 mM bis-Tris at pH 7 with varying amounts of MgCl$_2$.

Example 13

Successful Modification of Porous Membrane Substrates

Pyrogallol (PG) and tannic acid (TA) were used to modify poly(ether ether ketone) (PEEK) membranes. PEEK samples were modified with 2 mg/mL PG or TA in 100 mM bicine and 600 mM NaCl at pH 7.8 for 24 h. Since PEEK and PG- and TA-based coatings are composed of carbon and oxygen, a substrate-specific element was unavailable to confirm coating deposition. However, successful coating deposition was confirmed by X-ray photoelectron spectroscopy (XPS), observing the decrease in the carbon-to-oxygen (C/O) ratio, as determined by C1s and O1s signals for carbon and oxygen, respectively (Table 10). The experimental C/O ratio of samples decreased significantly following modification of PEEK with PG and TA. Compared to the theoretical value for the initial, bare substrate (6.333), the C/O ratios after modification approach the theoretical values for molecular PG or TA.

TABLE 10

Experimental (determined by XPS) and theoretical carbon-to-oxygen ratios (C/O)

| Substrate | Experimental C/O | Theoretical C/O* |
|---|---|---|
| PEEK | 6.001 | 6.333 |
| PEEK + PG | 2.526 | 2.000 |
| PEEK + TA | 1.894 | 1.652 |

*The theoretical C/O values are based on the molecular structure for PEEK, PG, and TA.

Figure 28:
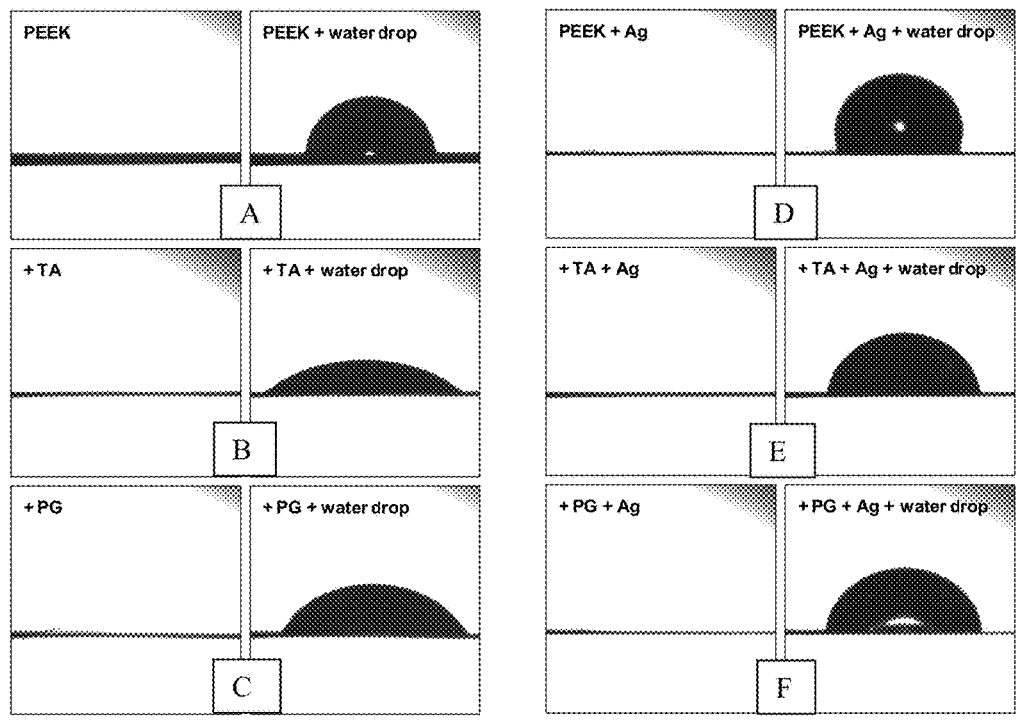
FIG. 28A. Bare PEEK, and water droplet on bare PEEK.
FIG. 28B. PEEK modified with TA, and water droplet on TA-modified PEEK.
FIG. 28C. PEEK modified with PG, and water droplet on PG-modified PEEK.
FIG. 28D. PEEK modified with $Ag^+$, and water droplet on bare PEEK incubated with $Ag^+$.
FIG. 28E. PEEK modified with TA and $Ag^+$, and water droplet on TA-modified PEEK reacted with $Ag^+$.
FIG. 28F. PEEK modified with PG and $Ag^+$, and water droplet on PG-modified PEEK reacted with $Ag^+$.

Macroscopic observations of water droplets on PEEK membranes indicated enhanced wettability following modification with PG or TA (FIG. 28). Moreover, the wettability appears to be reversed after subsequent incorporation of silver nanoparticles reduced in-situ, as seen by the reduced spreading of water droplets on treated surfaces (FIG. 28).

Figure 29:
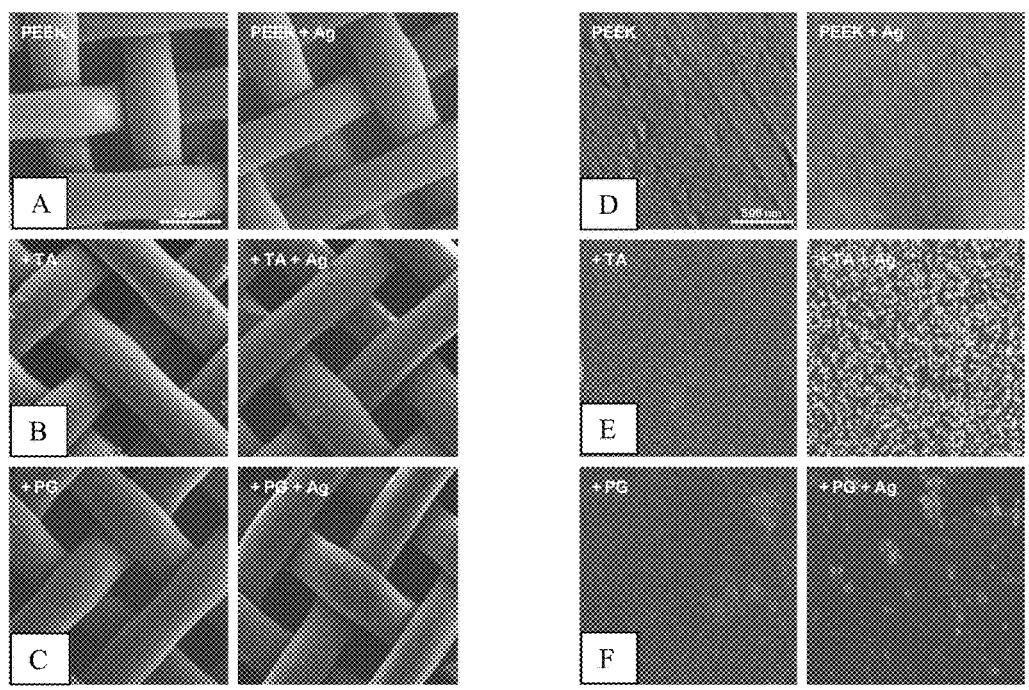
FIG. 29A. SEM micrographs of bare PEEK and PEEK modified with $Ag^+$ (scale bar is 50 μm).
FIG. 29B. SEM micrographs of TA-modified PEEK with and without $Ag^+$ (scale bar from A applies to B).
FIG. 29C. SEM micrographs of PG-modified PEEK with and without $Ag^+$ (scale bar from A applies to C).
FIG. 29D. SEM micrographs of bare PEEK and PEEK modified with Ag (scale bar is 500 nm).
FIG. 29E. SEM micrographs of TA-modified PEEK with and without $Ag^+$ (scale bar from D applies to E).
FIG. 29F. SEM micrographs of PG-modified PEEK with and without $Ag^+$ (scale bar from D applies to F).

Scanning electron microscopy (SEM) was employed to assess the surface morphologies of bare, PG- or TA-modified, and silver nanoparticle-functionalized PEEK membranes. The native porous structure of PEEK membranes is maintained following modification with PG and TA, both with and without further incorporation of silver nanoparticles (FIG. 29). The presence of silver nanoparticles on TA- and PG-modified PEEK membranes further confirms successful modification of the membranous material (FIG. 29).

Example 14

Comparison of Bacterial Viability on Coatings Based on Tannic Acid and Dopamine

Figure 30:
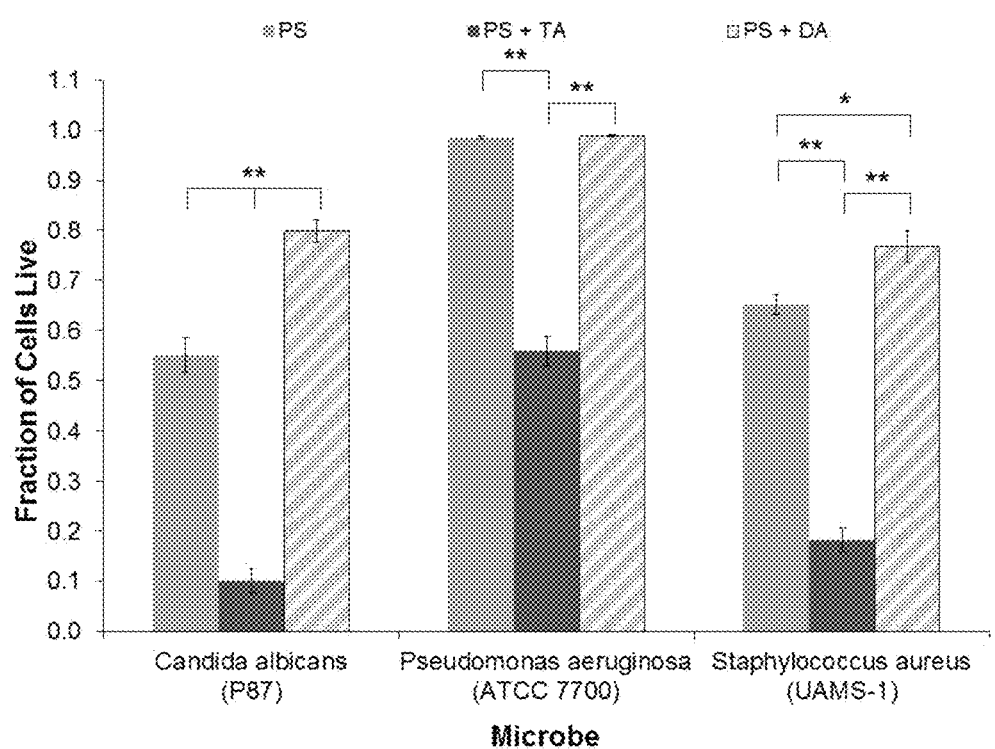
FIG. 30. Microbial viability on polystyrene (PS), TA-coated PS (PS+TA), and dopamine-coated PS (PS+DA). TA coatings were prepared using a 2 mg/mL solution of TA in 100 mM bicine, 600 mM NaCl at pH 7.8. DA coatings were prepared using a 2 mg/mL solution of DA in 10 mM Tris at pH 8.5. * $p<0.05$; ** $p<0.001$. *

Unmodified polystyrene (as opposed to tissue culture plastic) was modified with coatings derived from tannic acid (TA) and dopamine (DA). TA was coated via a 2 mg/mL solution containing 100 mM bicine and 600 mM NaCl at pH 7.8. DA was coated via a 2 mg/mL solution containing 10 mM Tris at pH 8.5. Polystyrene was coated with TA and DA for 24 h. Antimicrobial activity was tested against *Candida albicans* (fungus), *Pseudomonas aeruginosa* (Gram-negative bacteria), and *Staphylococcus aureus* (Gram-positive bacteria) (FIG. 30). Microbial specimens were seeded at a density of 1.5×10$^6$ colony forming units (CFU) per mL. After 24 h, microbial viability was tested by staining with Syto 9 (for live cells) and propidium iodide (for dead cells). The fractions of live and dead cells were determined based on the area of fluorescence associated with the live and dead stains.

Example 15

Figure 31:
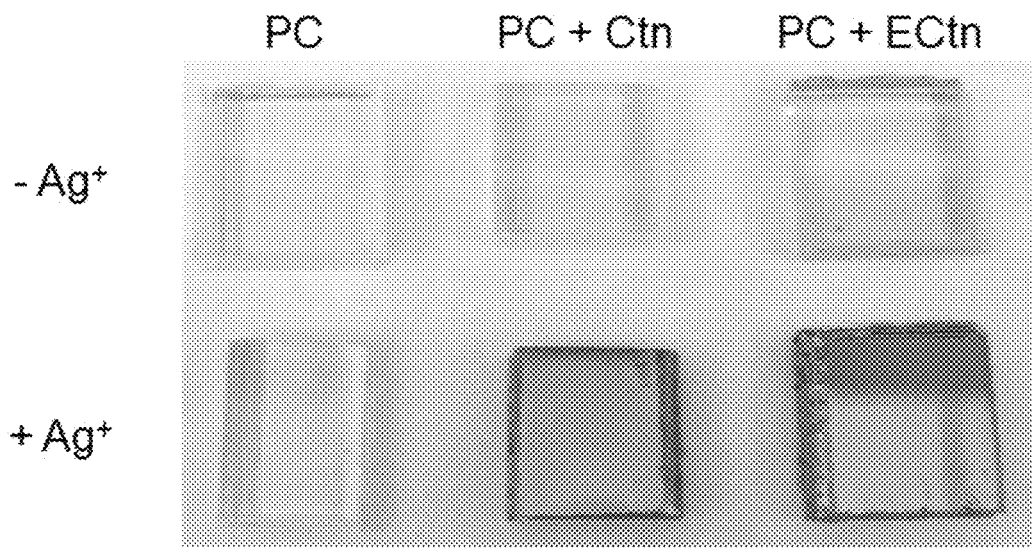
FIG. 31. Visualization of polycarbonate samples coated with catechin (Ctn) and epicatechin (ECtn).

Ability of (−)-epicatechin to Form Coatings Based on Conditions Used for (+)-catechin Catechin and epicatechin are stereoisomers. Until now, catechin has been investigated for its ability to form coatings. This example demonstrates that epicatechin is able to form coatings under conditions optimized for catechin. Solutions of (+)-catechin (Ctn) and (−) epicatechin (ECtn) were made at a concentration of 1 mg/mL in 100 mM bicine and 600 mM NaCl at pH 9. Polycarbonate (PC) samples were submerged in the solutions, rocked for 48 h, rinsed thoroughly with water, and dried with N$_2$ gas. The resulting coatings were stained with 100 mM solution of AgNO$_3$ for 48 h, rinsed thoroughly with water, and dried with $N_2$ gas. Images were then captured with a digital camera (FIG. 31).

Example 16

Removal of Heavy Metal Ions from Solution by Phenolic Coatings

Figure 32:
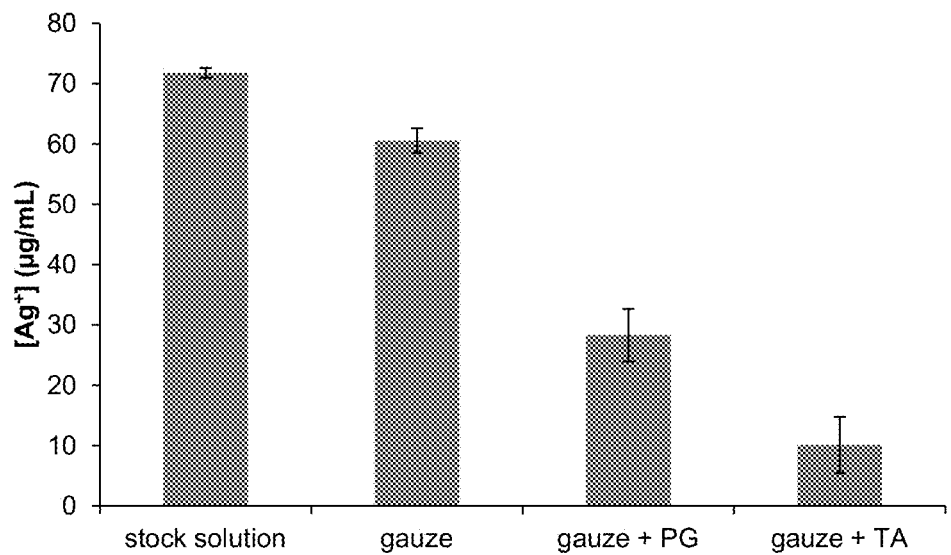
FIG. 32: Silver concentration of solutions before and after exposure to bare and phenolic-modified gauze (statistical significance of $p<0.05$ between gauze and stock solution, and $p<0.001$ for all other comparisons via one-way ANOVA).

Pyrogallol (PG) and tannic acid (TA) were used to modify cotton gauze samples weighing 140 mg±5%. Bare gauze and gauze modified with PG or TA were incubated in 10 mL of 0.42 mM (~72 µg/mL) $AgNO_3$ for 48 h, following which the solutions were analyzed for silver content using inductively-couple plasma mass spectrometry (ICP-MS). PG- and TA-modified gauze reduced silver concentration in solution, relative to unmodified gauze, by 53% and 83%, respectively (FIG. 32).

Example 17

Immobilization of Proteins and Enzymes onto Phenolic Coatings

Pyrogallol (PG) and tannic acid (TA) were used to modify $TiO_2$ samples under buffered saline conditions (pH 7.8, 100 mM bicine, 600 mM NaCl). Bare and phenolic-modified surfaces were exposed to 10 mg/mL lysozyme (from chicken egg white) solvated in water or buffered saline for 10 minutes under mild agitation. Lysozyme-treated samples were thoroughly rinsed with water and incubated in 0.1 M sodium dodecyl sulfate (SDS) for 30 minutes. The SDS incubation step was employed to screen out weakly-adhered enzyme from the surfaces. Lastly, the samples were thoroughly rinsed with water and dried under a nitrogen gas stream.

Figure 33:
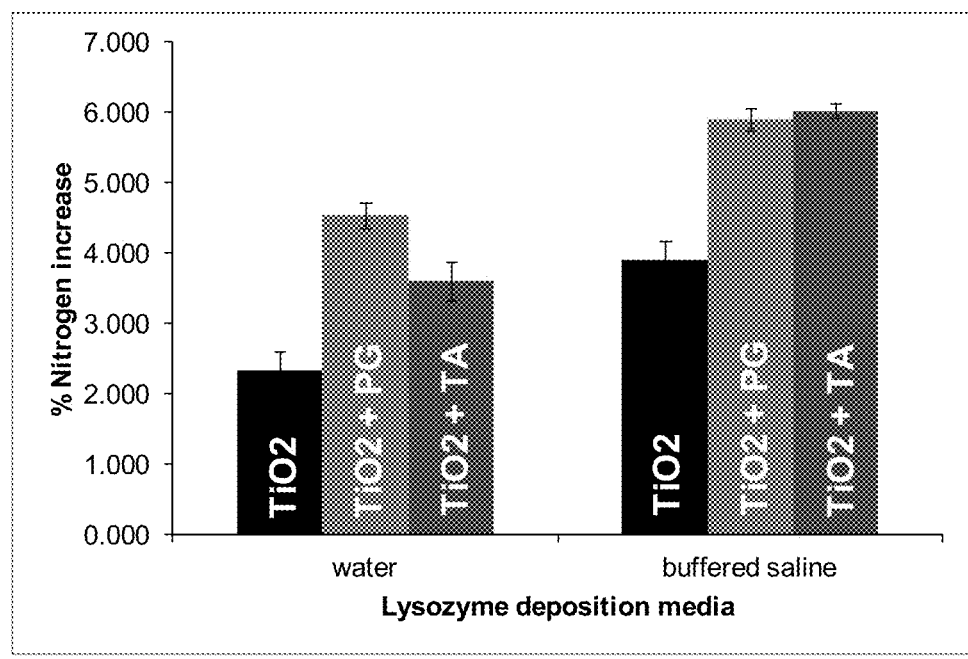
FIG. 33: Atomic percentage increase in the nitrogen content of $TiO_2$, $TiO_2$+PG, and $TiO_2$+TA surfaces modified with lysozyme in water or buffered saline.

Bare and modified substrates were analyzed using X-ray photoelectron spectroscopy (XPS) for presence of protein. The N1s signal was monitored, the increase of which corresponded to deposition of a protein on a surface (FIG. 33). $TiO_2$+PG surfaces yielded 95% and 51% increases in immobilized protein content when compared to bare $TiO_2$, using water and buffered saline for lysozyme deposition, respectively. $TiO_2$+TA surfaces yielded 54% and 55% increases in immobilized protein content when compared to bare $TiO_2$, using water and buffered saline for lysozyme deposition, respectively.

Example 18

Antioxidant Properties of Polyphenol-derived Coatings

Figure 34:
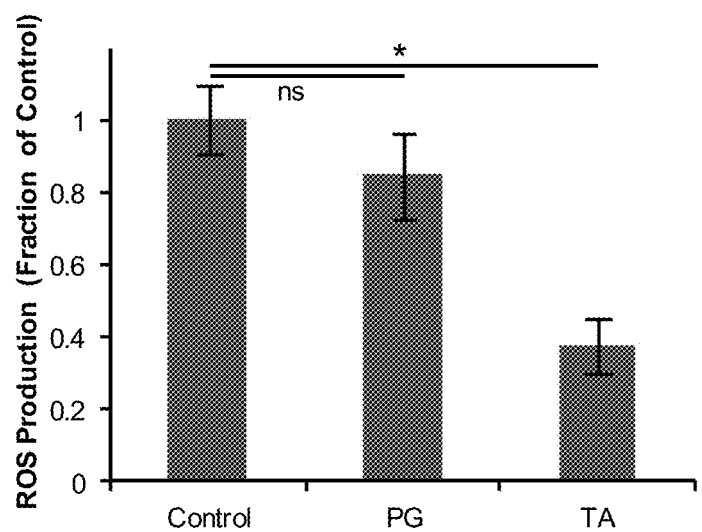
FIG. 34: Production of reactive oxygen species (ROS) in NIH 3T3 fibroblasts cultured on PG- and TA-modified surfaces as a fraction of bare polystyrene control.

Pyrogallol (PG) and tannic acid (TA) were used to modify polystyrene samples. Following modification, NIH 3T3 fibroblasts were cultured on bare and PG- or TA-treated surfaces. After 24 h of culture, the cells were loaded with 2',7'-dichlorofluorescin diacetate, followed by stimulation with a reactive oxygen species (ROS) inducing agent. The fraction of ROS production was determined as a function of fluorescence of the converted intracellular dichlorofluorescin (FIG. 34). It was noted that PG coatings were not able to substantially reduce ROS production relative to bare polystyrene controls. Tannic acid coatings, however, resulted in approximately 60% reduction in ROS production versus bare polystyrene controls.

Example 19

Anti-inflammatory Properties of Polyphenol-derived Coatings

Figure 35:
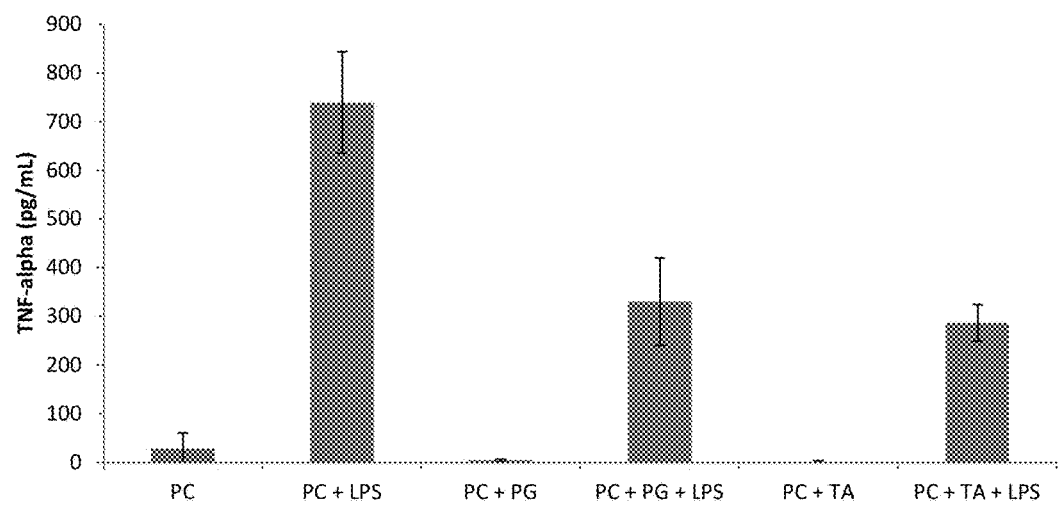
FIG. 35: TNF-α expression by RAW 264.7 murine monocytes on PC, PC+PG and PC+TA surfaces before and after stimulation with LPS.

Pyrogallol (PG) and tannic acid (TA) were used to modify polycarbonate (PC) samples under buffered saline conditions (pH 7.8, 100 mM bicine, 600 mM NaCl). RAW 264.7 murine monocytes were cultured on bare and PG- and TA-modified PC for 24 h, followed by stimulation with 1 µg/mL of lipopolysaccharides (LPS) derived from *Pseudomonas aeruginosa* for 1 h. The culture media was collected and analyzed for tumor necrosis factor alpha (TNF-α) using a commercially available ELISA kits (Invitrogen). TNF-α is a pro-inflammatory signaling molecule, elevated levels of which are directly correlated to enhanced inflammatory response. Stimulation with LPS results in upregulation of TNF-α production by RAW 264.7 monocytes when compared to non-stimulated controls. Incorporation of a PG or TA coating mitigates the observed TNF-α production by at least 60%, when compared to bare PC controls (FIG. 35).

In summary, we have described a facile, surface-independent, polyphenol coating whereby substrates of all kinds contacted with the coatings of the present invention are modified to support at least one functional reactive moiety on the substrate's surface. In some embodiments, the nitrogen-free phenolic compounds used in the present invention may be selected from epigallocatechin-3-gallate (EGCG), epigallocatechin (EGC) and epicatechin gallate (ECG), tannic acid, gallic acid and pyrogallol. The reactive moiety reacts with and is bound to the coated surface. The reactive moiety may comprise a metal ion selected from the group consisting of silver and gold ions, or a nucleophile selected from the group consisting of a protein or a thiol or amine containing polymer. Methods of use and kits comprising the coating are also included. In general, the method comprises contacting at least a portion of the substrate with the plant-derived or synthetic polyphenol coating of the present invention to provide a surface modified to support at least one reactive moiety.

The above description and attached figures are intended to be illustrative and not limiting of this invention. Many themes and variations of this invention will be suggested to one skilled in this and, in light of the disclosure. All such themes and variations are within the contemplation hereof. For instance, while this invention has been described in conjunction with the various exemplary embodiments outlined above, various alternatives, modifications, variations, improvements, and/or substantial equivalents, whether known or that rare or may be presently unforeseen, may become apparent to those having at least ordinary skill in the art. Various changes may be made without departing from the spirit and scope of the invention. Therefore, the invention is intended to embrace all known or later-developed alternatives, modifications, variations, improvements, and/ or substantial equivalents of these exemplary embodiments.

We claim:

1. A Method of forming a coating on a substrate surface, the method comprising contacting at least a portion of the substrate surface with an aqueous saline solution, comprising at least one salt selected from the group consisting of NaCl, MgCl2, CaCl2, CuCl2 with NaCl, ZnCl2 with NaCl and any combination thereof and an effective amount of one or more natural or synthetic polyphenols, pyrogallol, or gallic acid, wherein the polyphenols are selected from the group consisting of epigallocatechin-3-gallate (EGCG), epigallocatechin (EGC), epicatechin gallate (ECG), tannic acid, those extracted from green tea leaves, those extracted from cacao beans, those extracted from dark chocolate and those extracted from red wine, comprising 1) preparing the aqueous saline solution comprising the one or more polyphenols, pyrogallol, or gallic acid, and 2) applying the aqueous saline solution to the substrate; wherein the pH and the salt concentration are such that a coating forms on the substrate surface, which has a thickness greater that a coating formed under identical conditions, in the absence of the salt, further comprising the step of contacting the resulting coating with a reactive moiety, whereby the reactive moiety reacts with and becomes bound to the coating.

2. The method of claim 1, wherein the solution comprises NaCl.

3. The method of claim 1, wherein the solution is basic.

4. The method of claim 3, wherein the pH of the solution is about 7.8.

5. The method of claim 1, wherein the substrate surface is selected from the group consisting of titanium dioxide, silica, gold, polycarbonate, polysulfone, polytetrafluoroethylene, polystyrene, and stainless steel.

6. The method of claim 1, wherein the reactive moiety comprises a nucleophile or a metal ion.

7. The method of claim 6, wherein the metal ion is silver ion.

8. The method of claim 1, wherein the reactive moiety comprises silver ion (Ag+), and elemental silver becomes bound to the coating.

9. The method of claim 8, further comprising contacting the resulting coating with an alkanethiol, whereby the coating becomes superhydrophobic.

10. The method of claim 6, wherein the nucleophile is comprised of a protein or an amine- or thiol-functionalized polymer.

11. A coating on a surface substrate as produced by the method of claim 1.

12. A method of removing metal ions from a liquid, comprising contacting the liquid with the coating of claim 11, whereby at least some of the metal ions in the sample are captured by the coating and removed from the liquid.

13. The method of claim 12, wherein the metal ion is silver.

* * * * *